(12) United States Patent
Becker et al.

(10) Patent No.: US 9,669,376 B2
(45) Date of Patent: Jun. 6, 2017

(54) METHOD AND APPARATUS FOR DELIVERY OF SUBMICROLITER VOLUMES ONTO A SUBSTRATE

(71) Applicant: Agena Bioscience, Inc., San Diego, CA (US)

(72) Inventors: Thomas Becker, La Jolla, CA (US); Aaron A. Hanson, San Diego, CA (US)

(73) Assignee: AGENA BIOSCIENCE, INC., San Diego, CA (US)

( * ) Notice: Subject to any disclaimer, the term of this patent is extended or adjusted under 35 U.S.C. 154(b) by 0 days.

(21) Appl. No.: 14/656,267

(22) Filed: Mar. 12, 2015

(65) Prior Publication Data

US 2015/0182933 A1 Jul. 2, 2015

Related U.S. Application Data

(63) Continuation of application No. 13/683,214, filed on Nov. 21, 2012, now Pat. No. 8,999,266, which is a
(Continued)

(51) Int. Cl.
*B01J 19/00* (2006.01)
*B01L 3/02* (2006.01)
(Continued)

(52) U.S. Cl.
CPC ......... *B01J 19/0046* (2013.01); *B01L 3/0244* (2013.01); *B01L 3/0248* (2013.01); *B82Y 30/00* (2013.01); *G01N 1/10* (2013.01); *G01N 35/10* (2013.01); *G01N 35/1016* (2013.01); *B01J 2219/0059* (2013.01); *B01J 2219/00387* (2013.01); *B01J 2219/00527* (2013.01); *B01J 2219/00529* (2013.01);
(Continued)

(58) Field of Classification Search
CPC ........... B01L 3/5088; B01L 2300/0819; B01L 2300/089; B01L 2300/0829; B01L 2300/161; B01L 2300/163; B01L 2300/165; B01L 2300/1657; B01L 3/5085; B01J 19/004; B01J 2219/00529; B01J 2219/00585; B01J 2219/00608; B01J 2219/00619; B01J 2219/00659
See application file for complete search history.

(56) References Cited

U.S. PATENT DOCUMENTS 2,797,213 A 6/1957 Moore
3,046,118 A 7/1962 Schmidt
(Continued)

FOREIGN PATENT DOCUMENTS

DE 3221681 12/1993
DE 19617011 4/1996
(Continued)

OTHER PUBLICATIONS

Ardrey, "Electrospray mass spectrometry", Spectroscopy Europe 4(4):10-18 (1992).
(Continued)

*Primary Examiner* — Brian R Gordon
(74) *Attorney, Agent, or Firm* — Grant IP, Inc.

(57) ABSTRACT

A substrate for use in mass spectrometric analyzes having an array of target locations.

7 Claims, 7 Drawing Sheets

Related U.S. Application Data continuation of application No. 11/243,113, filed on Oct. 4, 2005, now abandoned, which is a continuation of application No. 10/037,356, filed on Oct. 24, 2001, now abandoned.

(60) Provisional application No. 60/244,404, filed on Oct. 30, 2000.

(51) Int. Cl.
    *B82Y 30/00*     (2011.01)
    *G01N 35/10*     (2006.01)
    *G01N 1/10*     (2006.01)
    *C40B 40/06*     (2006.01)
    *C40B 40/10*     (2006.01)
    *C40B 60/14*     (2006.01)
    *G01N 35/00*     (2006.01)
    *G01N 35/02*     (2006.01)

(52) U.S. Cl.
CPC .......... *B01J 2219/00585* (2013.01); *B01J 2219/00596* (2013.01); *B01J 2219/00605* (2013.01); *B01J 2219/00608* (2013.01); *B01J 2219/00612* (2013.01); *B01J 2219/00619* (2013.01); *B01J 2219/00659* (2013.01); *B01J 2219/00677* (2013.01); *B01J 2219/00686* (2013.01); *B01J 2219/00689* (2013.01); *B01J 2219/00691* (2013.01); *B01J 2219/00722* (2013.01); *B01J 2219/00725* (2013.01); *B01L 2200/0657* (2013.01); *C40B 40/06* (2013.01); *C40B 40/10* (2013.01); *C40B 60/14* (2013.01); *G01N 35/0099* (2013.01); *G01N 35/028* (2013.01); *G01N 35/1065* (2013.01); *G01N 2035/00158* (2013.01); *G01N 2035/1037* (2013.01); *Y10T 436/11* (2015.01); *Y10T 436/112499* (2015.01); *Y10T 436/119163* (2015.01); *Y10T 436/24* (2015.01); *Y10T 436/2575* (2015.01)

(56) References Cited

U.S. PATENT DOCUMENTS

| | | |
|---|---|---|
| 3,046,120 A | 7/1962 | Schmidt |
| 3,148,983 A | 9/1964 | Endermann et al. |
| 3,184,310 A | 5/1965 | Fritz et al. |
| 3,201,239 A | 8/1965 | Neugebauer et al. |
| 3,402,044 A | 9/1968 | Steinhoff et al. |
| 3,567,453 A | 3/1971 | Borden |
| 3,568,735 A | 3/1971 | Lancaster |
| 3,776,700 A | 12/1973 | Gallant |
| 3,782,197 A | 1/1974 | Grams |
| 3,807,235 A | 4/1974 | Lefkovitz |
| 3,813,544 A | 5/1974 | Franzen et al. |
| 3,999,689 A | 12/1976 | Ciantro et al. |
| 4,204,117 A | 5/1980 | Aberle et al. |
| 4,214,159 A | 7/1980 | Hillenkamp et al. |
| 4,243,887 A | 1/1981 | Hillenkamp et al. |
| 4,442,354 A | 4/1984 | Hurst et al. |
| 4,458,994 A | 7/1984 | Jain et al. |
| 4,461,328 A | 7/1984 | Kenney |
| 4,491,629 A | 1/1985 | Koike et al. |
| 4,548,245 A | 10/1985 | Crandell et al. |
| 4,550,069 A | 10/1985 | Pampalone |
| 4,554,839 A | 11/1985 | Hewett et al. |
| 4,725,677 A | 2/1988 | Koster et al. |
| 4,731,335 A | 3/1988 | Brigati |
| 4,735,778 A | 4/1988 | Maruyama et al. |
| 4,740,692 A | 4/1988 | Yamamoto et al. |
| 4,779,467 A | 10/1988 | Rainin et al. |
| 4,798,706 A | 1/1989 | Brigati |
| 4,844,298 A | 7/1989 | Ohoka et al. |
| 4,877,745 A | 10/1989 | Hayes et al. |
| 4,882,127 A | 11/1989 | Rosenthal et al. |
| 4,925,629 A | 5/1990 | Schramm |
| 4,931,400 A | 6/1990 | Jitsukawa |
| 4,948,442 A | 8/1990 | Manns |
| 4,952,518 A | 8/1990 | Johnson et al. |
| 5,000,921 A | 3/1991 | Hanaway et al. |
| 5,023,187 A | 6/1991 | Koebler et al. |
| 5,045,694 A | 9/1991 | Beavis et al. |
| 5,055,271 A | 10/1991 | Golias et al. |
| 5,055,408 A | 10/1991 | Higo et al. |
| 5,077,210 A | 12/1991 | Eigler et al. |
| 5,108,703 A | 4/1992 | Pfost et al. |
| 5,118,605 A | 6/1992 | Urdea |
| 5,118,937 A | 6/1992 | Hillenkamp et al. |
| 5,143,854 A | 9/1992 | Pirrung et al. |
| 5,171,989 A | 12/1992 | Williams et al. |
| 5,175,209 A | 12/1992 | Beattie et al. |
| 5,195,657 A | 3/1993 | Wells |
| 5,210,412 A | 5/1993 | Levis et al. |
| 5,221,518 A | 6/1993 | Mills |
| 5,262,128 A | 11/1993 | Leighton et al. |
| 5,279,796 A | 1/1994 | Parker et al. |
| 5,288,644 A | 2/1994 | Beavis et al. |
| 5,300,774 A | 4/1994 | Buttrill |
| 5,312,233 A | 5/1994 | Tanny et al. |
| 5,338,688 A | 8/1994 | Deeg et al. |
| 5,350,676 A | 9/1994 | Oberhardt et al. |
| 5,373,156 A | 12/1994 | Franzen |
| 5,376,788 A | 12/1994 | Standing et al. |
| 5,381,008 A | 1/1995 | Tanner et al. |
| 5,382,793 A | 1/1995 | Weinberger et al. |
| 5,399,501 A | 3/1995 | Pope et al. |
| 5,429,673 A * | 7/1995 | Peterson .......... C07F 7/10 106/285 |
| 5,439,649 A | 8/1995 | Tseung et al. |
| 5,457,041 A | 10/1995 | Ginaven et al. |
| 5,498,545 A | 3/1996 | Vestal |
| 5,503,980 A | 4/1996 | Cantor |
| 5,504,326 A | 4/1996 | Reilly et al. |
| 5,505,916 A | 4/1996 | Berry, Jr. |
| 5,506,348 A | 4/1996 | Pieles |
| 5,510,613 A | 4/1996 | Reilly et al. |
| 5,512,295 A | 4/1996 | Kornberg et al. |
| 5,514,548 A | 5/1996 | Krebber et al. |
| 5,525,812 A | 6/1996 | Bandzuch et al. |
| 5,547,835 A | 8/1996 | Koster |
| 5,550,004 A | 8/1996 | Honda |
| 5,558,983 A | 9/1996 | Simpson et al. |
| 5,561,029 A | 10/1996 | Fitzgerald et al. |
| 5,567,569 A | 10/1996 | Aviram et al. |
| 5,580,434 A | 12/1996 | Robotti et al. |
| 5,580,733 A | 12/1996 | Levis et al. |
| 5,589,136 A | 12/1996 | Northrup et al. |
| 5,591,969 A | 1/1997 | Park et al. |
| 5,599,500 A | 2/1997 | Jones |
| 5,601,982 A | 2/1997 | Sargent et al. |
| 5,605,662 A | 2/1997 | Heller et al. |
| 5,605,798 A | 2/1997 | Koster et al. |
| 5,607,816 A | 3/1997 | Fitzgerald et al. |
| 5,609,907 A | 3/1997 | Natan |
| 5,612,000 A | 3/1997 | Lemieux |
| 5,612,002 A | 3/1997 | Cody et al. |
| 5,614,153 A | 3/1997 | Homberg |
| 5,622,824 A | 4/1997 | Koster |
| 5,631,134 A | 5/1997 | Cantor |
| 5,643,800 A | 7/1997 | Tarantino et al. |
| 5,658,802 A | 8/1997 | Hayes et al. |
| 5,660,792 A | 8/1997 | Koike |
| 5,663,242 A | 9/1997 | Ghosh et al. |
| 5,670,322 A | 9/1997 | Eggers et al. |
| 5,670,381 A | 9/1997 | Jou et al. |
| 5,677,195 A | 10/1997 | Winkler et al. |
| 5,688,642 A | 11/1997 | Chrisey et al. |
| 5,691,141 A | 11/1997 | Koster |
| 5,700,642 A | 12/1997 | Monforte et al. |
| 5,716,825 A | 2/1998 | Hancock et al. |
| 5,742,049 A | 4/1998 | Holle et al. |
| 5,743,960 A | 4/1998 | Tisone |

(56) References Cited

U.S. PATENT DOCUMENTS

| | | | |
|---|---|---|---|
| 5,746,373 | A | 5/1998 | Sanada |
| 5,756,050 | A | 5/1998 | Ershow et al. |
| 5,757,392 | A | 5/1998 | Zhang |
| 5,770,151 | A | 6/1998 | Roach et al. |
| 5,770,272 | A | 6/1998 | Biemann et al. |
| 5,770,860 | A | 6/1998 | Franzen |
| 5,777,324 | A | 7/1998 | Hillenkamp |
| 5,795,714 | A | 8/1998 | Cantor et al. |
| 5,807,522 | A | 9/1998 | Brown et al. |
| 5,812,272 | A | 9/1998 | King et al. |
| 5,828,063 | A | 10/1998 | Koster et al. |
| 5,830,655 | A | 11/1998 | Monforte et al. |
| 5,837,860 | A | 11/1998 | Anderson et al. |
| 5,851,765 | A | 12/1998 | Koster |
| 5,854,486 | A | 12/1998 | Dreyfus |
| 5,864,137 | A | 1/1999 | Becker et al. |
| 5,869,240 | A | 2/1999 | Patterson |
| 5,869,242 | A | 2/1999 | Kamb |
| 5,872,003 | A | 2/1999 | Koster |
| 5,872,010 | A | 2/1999 | Karger et al. |
| 5,885,775 | A | 3/1999 | Haff et al. |
| 5,894,063 | A | 4/1999 | Hutchens et al. |
| 5,900,481 | A | 5/1999 | Lough et al. |
| 5,925,520 | A | 7/1999 | Tully et al. |
| 5,927,547 | A | 7/1999 | Papen et al. |
| 5,928,906 | A | 7/1999 | Koster et al. |
| 5,955,729 | A | 9/1999 | Nelson et al. |
| 5,957,167 | A | 9/1999 | Feygin |
| 5,965,363 | A | 10/1999 | Monforte et al. |
| 5,969,350 | A | 10/1999 | Kerley et al. |
| 5,981,185 | A | 11/1999 | Matson et al. |
| 5,985,356 | A | 11/1999 | Schultz et al. |
| 5,998,103 | A * | 12/1999 | Zhang .................. G03F 7/085 427/207.1 |
| 6,022,688 | A | 2/2000 | Jurinke et al. |
| 6,024,925 | A | 2/2000 | Little et al. |
| 6,040,193 | A | 3/2000 | Winkler et al. |
| 6,043,031 | A | 3/2000 | Koster et al. |
| 6,051,378 | A | 4/2000 | Monforte et al. |
| 6,063,339 | A | 5/2000 | Tisone et al. |
| 6,066,448 | A * | 5/2000 | Wohlstadter ........... G01N 21/66 204/400 |
| 6,074,823 | A | 6/2000 | Koster et al. |
| 6,079,283 | A | 6/2000 | Papen et al. |
| 6,083,762 | A | 7/2000 | Papen et al. |
| 6,090,558 | A | 7/2000 | Butler et al. |
| 6,101,946 | A | 8/2000 | Martinsky |
| 6,103,518 | A | 8/2000 | Leighton |
| 6,104,028 | A | 8/2000 | Hunter et al. |
| 6,110,426 | A | 8/2000 | Shalon et al. |
| 6,111,251 | A | 8/2000 | Hillenkamp |
| 6,116,297 | A | 9/2000 | Feygin |
| 6,121,048 | A | 9/2000 | Zaffaroni et al. |
| 6,133,436 | A | 10/2000 | Koster et al. |
| 6,136,269 | A | 10/2000 | Winkler et al. |
| 6,146,854 | A | 11/2000 | Koster et al. |
| 6,159,425 | A | 12/2000 | Edwards et al. |
| 6,193,939 | B1 | 2/2001 | Kozlowski |
| 6,194,144 | B1 | 2/2001 | Koster |
| 6,197,498 | B1 | 3/2001 | Koster |
| 6,207,370 | B1 | 3/2001 | Little et al. |
| 6,221,601 | B1 | 4/2001 | Koster et al. |
| 6,221,605 | B1 | 4/2001 | Koster |
| 6,225,061 | B1 | 5/2001 | Becker et al. |
| 6,225,450 | B1 | 5/2001 | Koster et al. |
| 6,235,478 | B1 | 5/2001 | Koster |
| 6,238,871 | B1 | 5/2001 | Koster |
| 6,258,538 | B1 | 7/2001 | Koster et al. |
| 6,265,716 | B1 | 7/2001 | Hunter et al. |
| 6,268,131 | B1 | 7/2001 | Kang et al. |
| 6,268,144 | B1 | 7/2001 | Koster |
| 6,269,846 | B1 | 8/2001 | Overbeck et al. |
| 6,277,573 | B1 | 8/2001 | Koster |
| 6,287,872 | B1 | 9/2001 | Schurenberg et al. |
| 6,287,972 | B1 | 9/2001 | Ziger et al. |
| 6,300,076 | B1 | 10/2001 | Koster |
| 6,303,309 | B1 | 10/2001 | Jurinke et al. |
| 6,309,891 | B1 | 10/2001 | Shalon et al. |
| 6,322,970 | B1 | 11/2001 | Little et al. |
| 6,342,396 | B1 | 1/2002 | Perrin et al. |
| 6,355,487 | B2 | 3/2002 | Kowallis |
| 6,376,044 | B1 | 4/2002 | Jarrell et al. |
| 6,387,628 | B1 | 5/2002 | Little et al. |
| 6,399,394 | B1 | 6/2002 | Dahm et al. |
| 6,406,670 | B1 | 6/2002 | Earley et al. |
| 6,419,881 | B1 | 7/2002 | Weinberg et al. |
| 6,423,966 | B2 | 7/2002 | Hillenkamp et al. |
| 6,428,955 | B1 | 8/2002 | Koster et al. |
| 6,485,913 | B1 | 11/2002 | Becker et al. |
| 6,500,621 | B2 | 12/2002 | Koster |
| 6,506,611 | B2 | 1/2003 | Bienert et al. |
| 6,558,902 | B1 | 5/2003 | Hillenkamp |
| 6,565,813 | B1 * | 5/2003 | Garyantes ........... B01F 13/0071 422/553 |
| 6,566,055 | B1 | 5/2003 | Monforte et al. |
| 6,569,385 | B1 | 5/2003 | Little et al. |
| 6,589,485 | B2 | 7/2003 | Koster |
| 6,602,662 | B1 | 8/2003 | Koster et al. |
| 6,605,257 | B1 | 8/2003 | Nakazawa et al. |
| 6,610,253 | B2 | 8/2003 | Kennedy et al. |
| 6,629,626 | B1 | 10/2003 | Horsman et al. |
| 6,632,641 | B1 * | 10/2003 | Brennan ................ C12Q 1/686 435/287.2 |
| 6,635,452 | B1 | 10/2003 | Monforte et al. |
| 6,670,609 | B2 | 12/2003 | Franzen et al. |
| 6,723,569 | B1 | 4/2004 | Moore et al. |
| 6,730,517 | B1 | 5/2004 | Koster et al. |
| 6,769,760 | B1 | 8/2004 | Kuo et al. |
| 6,812,455 | B2 | 11/2004 | Hillenkamp |
| 6,835,352 | B2 | 12/2004 | Ito et al. |
| 6,858,184 | B2 | 2/2005 | Pelrine et al. |
| 6,861,214 | B1 | 3/2005 | Rampal et al. |
| 6,881,379 | B1 * | 4/2005 | Bredehorst .......... B01J 19/0046 422/412 |
| 6,902,705 | B1 * | 6/2005 | Caillat .............. G01N 33/5438 422/500 |
| 7,144,554 | B1 | 12/2006 | Gulla et al. |
| 7,160,687 | B1 * | 1/2007 | Kapur .................. B01L 3/5027 356/300 |
| 7,256,046 | B2 | 8/2007 | Nebuloni et al. |
| 7,267,800 | B2 | 9/2007 | Takii et al. |
| 7,285,422 | B1 | 10/2007 | Little et al. |
| 7,473,031 | B2 * | 1/2009 | Wolkin ................. B82Y 15/00 374/12 |
| 7,521,245 | B1 | 4/2009 | Osgood |
| 7,642,097 | B2 * | 1/2010 | Kronick ................. B01L 3/508 206/456 |
| 2001/0008615 | A1 | 7/2001 | Little et al. |
| 2001/0049148 | A1 | 12/2001 | Wolk et al. |
| 2001/0049149 | A1 | 12/2001 | Kennedy et al. |
| 2001/0055811 | A1 | 12/2001 | Hillenkamp |
| 2002/0005478 | A1 | 1/2002 | Hillenkamp |
| 2002/0009394 | A1 | 1/2002 | Koster et al. |
| 2002/0018999 | A1 | 2/2002 | Henriksson et al. |
| 2002/0040130 | A1 | 4/2002 | Braun |
| 2002/0041829 | A1 | 4/2002 | Kowallis |
| 2002/0051971 | A1 | 5/2002 | Stuelpnagel et al. |
| 2002/0076723 | A1 | 6/2002 | Virtanen |
| 2002/0098115 | A1 | 7/2002 | Fawcett et al. |
| 2002/0102725 | A1 | 8/2002 | Zabarovsky et al. |
| 2002/0109085 | A1 | 8/2002 | Hillenkamp et al. |
| 2002/0119578 | A1 | 8/2002 | Zaffaroni et al. |
| 2002/0142483 | A1 | 10/2002 | Yao et al. |
| 2002/0155587 | A1 | 10/2002 | Opalsky et al. |
| 2002/0159918 | A1 | 10/2002 | Tseng et al. |
| 2003/0003465 | A1 | 1/2003 | Little et al. |
| 2003/0017469 | A1 | 1/2003 | Risinaer et al. |
| 2003/0022225 | A1 | 1/2003 | Monforte et al. |
| 2003/0033091 | A1 | 2/2003 | Opalsky et al. |
| 2003/0036057 | A1 | 2/2003 | Braun et al. |
| 2003/0096426 | A1 | 5/2003 | Little et al. |
| 2003/0111494 | A1 | 6/2003 | Lin et al. |
| 2003/0113233 | A1 | 6/2003 | Nanthakumar |
| 2003/0113745 | A1 | 6/2003 | Monforte et al. |

(56) References Cited

U.S. PATENT DOCUMENTS

| | | | |
|---|---|---|---|
| 2003/0124735 A1 | 7/2003 | Nanthakumar et al. |
| 2003/0129589 A1 | 7/2003 | Koster et al. |
| 2003/0148528 A1 | 8/2003 | Hillenkamp |
| 2003/0180148 A1 | 9/2003 | Weng |
| 2003/0180749 A1 | 9/2003 | Koster et al. |
| 2003/0190644 A1 | 10/2003 | Braun et al. |
| 2003/0207297 A1 | 11/2003 | Koster et al. |
| 2003/0215368 A1 | 11/2003 | Ito et al. |
| 2003/0220844 A1 | 11/2003 | Manellos et al. |
| 2003/0224418 A1 | 12/2003 | Braun et al. |
| 2003/0228594 A1 | 12/2003 | Koster et al. |
| 2004/0037748 A1 | 2/2004 | Hasan et al. |
| 2004/0062686 A1 | 4/2004 | Ganz |
| 2004/0072365 A1 | 4/2004 | Rose et al. |
| 2004/0126895 A1 | 7/2004 | Overbeck et al. |
| 2005/0053521 A1 | 3/2005 | Hirayama |
| 2005/0063866 A1 | 3/2005 | Moor |
| 2005/0136534 A1 | 6/2005 | Austin et al. |
| 2005/0281707 A1 | 12/2005 | Nakaya |
| 2006/0024841 A1 | 2/2006 | Yao et al. |
| 2008/0008874 A1 | 1/2008 | Little et al. |
| 2008/0047368 A1 | 2/2008 | Marziali |
| 2008/0169184 A1* | 7/2008 | Brown ............... B01L 3/5027 204/164 |
| 2008/0318310 A1 | 12/2008 | Dufresne |
| 2009/0130745 A1 | 5/2009 | Williams et al. |
| 2009/0180931 A1 | 7/2009 | Silbert et al. |
| 2013/0017128 A1 | 1/2013 | Silbert et al. |
| 2013/0079247 A1 | 3/2013 | Yao et al. |
| 2015/0037213 A1 | 2/2015 | Silbert et al. |

FOREIGN PATENT DOCUMENTS

| | | |
|---|---|---|
| DE | 19618032 | 5/1996 |
| DE | 19628178 | 7/1996 |
| DE | 19731479 | 7/1997 |
| DE | 19754978 | 12/1997 |
| EP | 0339781 | 11/1989 |
| EP | 0396116 | 11/1990 |
| EP | 0500506 | 8/1992 |
| EP | 0543550 | 5/1993 |
| EP | 0268237 | 5/1998 |
| EP | 1164203 | 12/2001 |
| EP | 1262564 | 12/2002 |
| EP | 1271609 | 2/2003 |
| FR | 2597260 | 10/1987 |
| GB | 2017105 | 10/1979 |
| GB | 2233654 | 1/1991 |
| GB | 2312782 | 11/1997 |
| GB | 2332273 | 6/1999 |
| JP | 2215399 | 8/1990 |
| JP | A-8-233710 | 9/1996 |
| JP | 8290377 | 11/1996 |
| JP | 63230086 | 9/1998 |
| JP | 2001-033463 | 2/2001 |
| JP | 2001-296303 | 10/2001 |
| JP | 2007-147656 | 6/2007 |
| WO | WO 84/02579 | 7/1984 |
| WO | WO 88/05074 | 7/1988 |
| WO | WO 89/09406 | 10/1989 |
| WO | WO 89/10786 | 11/1989 |
| WO | WO 89/11270 | 11/1989 |
| WO | WO 89/12624 | 12/1989 |
| WO | WO 90/01564 | 2/1990 |
| WO | WO 92/07879 | 5/1992 |
| WO | WO 92/13629 | 8/1992 |
| WO | WO 93/09668 | 5/1993 |
| WO | WO 93/14108 | 7/1993 |
| WO | WO 94/03774 | 2/1994 |
| WO | WO 94/11529 | 5/1994 |
| WO | WO 94/11530 | 5/1994 |
| WO | WO 94/11735 | 5/1994 |
| WO | WO 94/16101 | 7/1994 |
| WO | WO 94/21822 | 9/1994 |
| WO | WO 94/27719 | 12/1994 |
| WO | WO 95/04524 | 2/1995 |
| WO | WO 95/11755 | 5/1995 |
| WO | WO 95/13538 | 5/1995 |
| WO | WO 95/25116 | 9/1995 |
| WO | WO 95/25175 | 9/1995 |
| WO | WO 95/30773 | 11/1995 |
| WO | WO 95/35505 | 12/1995 |
| WO | WO 96/02836 | 2/1996 |
| WO | WO 96/19587 | 6/1996 |
| WO | WO 96/29431 | 9/1996 |
| WO | WO 96/32504 | 10/1996 |
| WO | WO 96/36731 | 11/1996 |
| WO | WO 97/08306 | 3/1997 |
| WO | WO 97/16699 | 5/1997 |
| WO | WO 97/33000 | 9/1997 |
| WO | WO 97/37041 | 10/1997 |
| WO | WO 97/42348 | 11/1997 |
| WO | WO 97/43617 | 11/1997 |
| WO | WO 98/03257 | 1/1998 |
| WO | WO 98/05965 | 2/1998 |
| WO | WO 98/12355 | 3/1998 |
| WO | WO 98/20019 | 5/1998 |
| WO | WO 98/20020 | 5/1998 |
| WO | WO 98/20166 | 5/1998 |
| WO | WO 98/22541 | 5/1998 |
| WO | WO 98/26179 | 6/1998 |
| WO | WO 98/34116 | 8/1998 |
| WO | WO 98/39481 | 9/1998 |
| WO | WO 99/12040 | 3/1999 |
| WO | WO 99/36760 | 7/1999 |
| WO | WO 99/57318 | 11/1999 |
| WO | WO 00/08474 | 2/2000 |
| WO | WO 00/25923 | 5/2000 |
| WO | WO 00/56446 | 9/2000 |
| WO | WO 00/60361 | 10/2000 |
| WO | WO 01/19518 | 3/2001 |
| WO | WO 02/055199 | 7/2002 |
| WO | WO 03/087410 | 10/2003 |

OTHER PUBLICATIONS

Arshady, Reza. Beaded polymer supports and gels: I. Manufacturing techniques, Journal of Chromatography, 586:181-197 (1991).

Arshady. Reza, Beaded polymer supports and gels: II. Physico-chemical criteria and functionalization, Journal of Chromatography, 586:199-219 (1991).

Asseline et al. "New Solid-Phase for Automated Synthesis of Oligonucleotides Containing an Amino-Alkyl Linker at Their 3'-End," Tetrahedron Letters 31(1: 81-84 (1990).

Batista-Viera et al., A new method for reversible immobilization of thiol biomolecules based on solid-phase bound thiolsulfonate groups, App. Biochem and Biotech,31 :175-195 (1991).

Beattie et al., "Synthesis and use of oligonucleotide libraries," Chemical Abstracts 123:1172 (1995).

Berenkamp et al., "Infrared MALDI Mass Spectometry of large Nucleic Acids" Science 281:260-262 (1998).

Bonftls, E. and N.T. Thuong. "Solid Phase Synthesis of 5', 3'Bifunctional Oligodeoxyribonucleotides Bearing a Masked Thiol Group at the 3'-End," Tetrahedron Letters 32(26): 3053-3056 (1991).

Braun et al., "Improved Analysis of Microsatellites Using Mass Spectrometry", Genomics 46:18-23 (1997).

Broach et al., "High Throughput Screening for Drug Discovery", Nature, 384(Suppl 7):14-16, 1996.

Brown et al., "A single-bead decode strategy using electrospray ionization mass spectrometry and a new photo labile linker: 3-amino-3-(2-nitrophenyl) propionic acid", Mol. Diversity 1:4-12 (1995).

Brummel et al. "Evaluation of mass spectrometric methods applicable to the direct analysis of non-peptide bead-bound combinatorial libraries", Anal. Chem., 1996, v. 68, pp. 237-242.

Burbaum et al., "New Technologies for High-Throughput Screening" Curro Opin Chem. Biol. 1:72-78, 1997.

Chrisey et al., Covalent attachment of synthetic DNA to self-assembled monolayer films, Nucl. Acids Res. 24:3031-3039 (1996).

(56) References Cited

OTHER PUBLICATIONS

Chrisey et at, Fabrication of patterned DNA surfaces, Nucl. Acids. Res. 24:3040-3047 (1996).
Church et al., "Multiplex DNA Sequencing", Science 240:185-188 (1988).
Crain, "Mass spectrometric techniques in nucleic acid research", Mass Spectr. Rev. 9:505-554 (1990).
Dai, Yugin, et al., Two-Layer Sample Preparation: A Method for MALDJ-MS Analysis of Complex Peptide and Protein Mixtures, Analytical. Chemistry, (1999), 1087-1097 71(5), American Chemical Society.
Day et al., "Immobilization of polynucleotides on magnetic particles," Biochem. J. 278: 735-740 (1991).
Debitsudo, A. "121 :83891 9 Preparation of nucleotide thioalkyl esters and monomolecular membrane" Chemical Abstracts 121: 1166 (1994).
Debitsudo, A. "121:109581 h Preparation of oligonucleotide monolayer," Chemical Abstracts 121: 1163:1163 (1994).
Debitsudo, A. "122:291447q Organic super-thin fim of oligonucleotide derivative and method for its preparation," Chemical Abstracts 122: 1100 (1995).
Ehring, H. et al., "Photochemical versus thermal mechanisms in matrix-assisted laser desorption/ionization probed by back side desorption", Rapid Comm. in Mass Spect. 10:821-824 (1996).
Emmett, M.R. and R.M. Caprioli. "Micro-Electrospray Mass Spectrometry: Ultra- High-Sensitivity Analysis of Peptides and Proteins," J. Am. Soc. Mass Spectrometry 5: 605-613 (1994).
Fast Evaporation, http://www.chemistry.wustl.edu/-msf/damon/samp_fast13 evap.html, pp. 1-2, Sample Preparation-Fast Evaporation. Downloaded Dec. 8, 2004.
Fernandes. P.R. "Letter from the Society President", J Biornol. Screening, 2(1): 1-9, 1997.
Frank and Koster, DNA chain length and the influence of base composition on electrophoretic mobility of oligodeoxyribonucleotides in polyacrylamide-gels, Nucl. Acids Res. 6:2069-2087 (1979).
Greene and Wuts, Protective Groups in Organic Synthesis, 2nd Edition, Wiley & Sons (1991).
Hayashi et al., Immobilization of thiol proteases onto porous poly(vinyl alcohol) beads, Polymer Journal, 25:5,489-497(1993).
Hillenkamp and Ehring, Laser desorption mass spectrometry Part 1: Basic mechanisms and techniques, Mass Spectrometry in the Biological Sciences: A tutorial, pp. 165-179 (1992).
Hillenkamp et al., Matrix assisted UV-laser desorption lionization: A new approach to mass spectrometry of large biomolecules, Bio mass Spectr., Burlingame and McCloskey (eds.), pp. 49-61, Elsevier Science Publishers B.V., Amsterdam (1989).
Hofstadler et al. "Capillary Electrophoresis—Electrospray Ionization Fourier Transform Ion Cyclotron Resonance Mass Spectrometry for Direct Analysis of Cellular Proteins," Anal. Chem. 67: 1477-1480 (1995).
IUPACE-IUB Commission on Biochemical Nomenclature Symbols for Amino-Acid Derivatives and Peptides Recommenations (1971), Biochemistry, 11(9):1726-1731.
Janzen et al., High Throughput Screening as a Discovery Tool in the Pharmaceutical Industry, Lab Robotics Automation (LRA), 8:261-265, 1996.
Jespersen et al. "Attomole Detection of Proteins by Matrix-assisted Laser Desorption/Ionization Mass Spectrometry with the Use of Picolitre Vials," Rapid Communications in Mass Spectrometry 8(8): 581-584 (1994).
Jett et al., "High-Speed DNA Sequencing: An Approach Based Upon fluorescence Detection of Single Molecules" J. Bio Strut & Dynam. 7(2):301-09 (1989).
Koster et al., "A strategy for rapid and efficient DNA sequencing by mass spectrometry", Nature Bio 14:1123-1128 (1996).
Koster et al., "Well-Defined Insoluble Primers for the Enzymatic Synthesis of Oligo and Polynucleotides", Hoppe-Seyler's Z. Physiol. Chern. 359:1579-1589 (1978).
Koster et at. N-acyl protecting groups for deoxynucleotides: A quantitative and comparative study, Tetrahedron 37:363-369 (1981).
Koster et at. Oligonucleotide synthesis and multiplex DNA sequencing using chemiluminescent detection, Nucl. Acids Res .• Symposium Series No. 24:318-321, (1991).
Kozal et al., "Extensive Polymorph isms Observed in HIV-1 Clade B Protease Gene Using High-Density Oligonucleotide Arrays," Nature Medicine, vol. 2, No. 7, pp. 753-159, (1996).
Landegren et al.. "DNA Diagnostics-Molecular techniques and automation", Science 242:229-237 (1988).
Lee, et al., Direct Measurement of the Forces Between Complementary Strands of DNA, Science, vol. 266, Nov. 4, 1994, 771-773.
Lennon, J. and Glish, G., "A transmission geometry probe for MALDI", Poster Abstract from Proceedings of the ASMS Conference on Mass Spectrometry and Allied Topics (1996).
Li et al., "High-Resolution MALDI Fourier Transform Mass Spectrometry of Oligonucleotides", Anal Chem. 68(13):2090-2096 (1996).
Li et al. "Analysis of Single Mammalain Cell Lysates by Mass Spectrometry," J. Am. Chem. Soc. 118: 11662-11663 (1996).
Little et al., "Direct detection of synthetic and biologically generated double stranded DNA by MALDI-TOF MS", J. Mass Spec 17:1-8 (1997).
Little et al., "MALDI on a Chip: Analysis of Arrays of Low-Femtomole to Sub-femto-mole Quantities of Synthetic Oligonucleotides and DNA Diagnostic Products Dispensed by a Piezoelectric Pipet", Anal Chem. 69:4540-4546 (1997).
Little et al., "Mass spectrometry from miniaturized arrays for full comparative DNA analysis", Nature Med 3(12):1413-1416 (1997).
Lyttle et al., "Versatile Linker Chemistry for Synthesis of 3'-Modified DNA", Chem. Abst., 128(18):314 (1997).
M.C. Fitzgerald et al., "The promise of matrix-assisted laser desorption-ionization (MALDI) mass spectrometry," Annu. Rev. Biophys. Biomol. Struct. 24: 117-140 (1995).
Manoharan et al., "A 2'-O-thiol Tether in the Ribose Moiety of Nucleic Acids for Conjugation Chemistry", Gene, 149: 147-156 (1994).
Martin, "New technologies for large-genome sequencing", Genome 31 :1073-1080 (1969).
McCray and Trentham, "Properties and uses of photo reactive caged compounds", Annu. Rev. Biophys. Biophys. Chern. 18:239-270 (1989).
Microdrop Gmbh. Nordersted. Germany, Autodrop system printed from the internet on Sep. 16, 1999.
Moini et al., "A moving belt device to couple high-performance liquid chromatography and chemical reaction interface mass spectrometry", Bio Mass Spect 20:308-312 (1991).
NanoPrintTM Microarrayer 60 and 210 slide capacity with plate product information download from http://www.arrayit.com/Products/Microarrayl/NanoPrint/nanoprint.html on May 17, 2007.
Nelson et al., Time-of-flight mass spectrometry of nucleic acids by laser ablation and ionization from a frozen aqueous matrix, Rapid Communications in Mass Spectrometry 4:348-351 (1990).
Nelson et al., "Volatilization of high molecular weight DNA by pulsed laser ablation of frozen aqueous solutions", Science 246: 1585-1587 (1989).
Nicola, Anthony J., et al., Application of the Fast-evaporation Sample Preparation Method for improving Quantification of Angiotensin II by Matrix-assisted Laser Desorption/Ionization, Rapid Communications in Mass Spectrometry, (1995), 1164-1171, 9, John Wiley & Sons, Ltd.
Nordhoff et al., "Ion stability of nucleic acids in infrared matrix-assisted laser desorption/ionization mass spectrometry", Nuc Acids Res. 21(15):3347-3357 (1993).
Nordhoff et al., "Matrix-assisted laser desorption/ionization mass spectrometry of nucleic acids with wavelength in the ultraviolet and infrared", Rapid Comm. Mass Spectrom. 6:771-776 (1992).
O'Donnell et al., "Mass Array as an enabling technology for the industrial-scale analysis of DNA", Genetic Engineering News 17(21) (1997).
O'Donnell et al., "High-Density, Covalent Attachment of DNA to Silicon Wafers for Analysis by MALDI-TOF Mass Spectrometry", Analytical Chemistry 69(13):2438-2443 (1991).

(56) References Cited

OTHER PUBLICATIONS

O'Donnell-Maloney et al., "The development of micro fabricated arrays for DNA sequencing and analysis" TIBTECH 14:401-407 (1996).

O'Donnell-Maloney et al.. "Micro fabrication and array technologies for DNA sequencing and diagnostics", Genetic Analysis: Bimolecular Engineering 13:151-157 (1996).

On-Probe Decontamination for MALDI Samples, pp. 1-2, http://www.chemistry.msu.edu/faculty/bruening/onprobepurification.htm, Matrix. Downloaded Dec. 8, 2004.

Overberg et al., "Laser desorption mass spectrometry: part II performance and applications of matrix-assisted laser desorption/ionization of large biomolecules", Mass Spect in the Biolog Science: A Tutorial 181-197 (1992).

Pon et al., "Derivatization of Controlled Pore Glass Beads for Solid Phase Oligonucleotide Synthesis" Bio Technique 6(8}: 768-770 773-775 (1988).

Product brochure for LAMMA 500 Laser Microprobe Mass Analyzer, (Leybold-Heraeus GMBH), 3-15 (1983).

Rolfs et al., PCR: Clinical Diagnostics and Research. Springer-Verlag (1992).

Ruppert et al., "A rapid and high throughput method for plasmid isolations". Presented: Automation in Mapping and DNA Sequencing Conference. Aug. 31-Sep. 2, 1994.

Ruppert et al.. "Preparation of plasmid DNA as Sequencing Templates in a Microtiter Plate Format", Paper presented. Cold Spring Harbor Laboratory May 1995.

Schober, et al., Accurate High-Speed Liquid Handling of Very Small Biological Samples, BiotechniQues, (1993) 15(2):324-329.

Schram. Karl H., "Mass spectrometry of nucleic acid components", Bio Appl of Mass Spect. 34:203-287 (1990).

SEQUENOM Advances the Industrial Genomics Revolution with the Launch of Its DNA MassArmy.TM. Automated Process Line, Press Release: Sep. 28, 1998. http://www.seQuenom.comlpressrelease.com.

Sequenom Inc. MassARRAY System Promotional Folder 2007.

SEQUENOM Reports DNA MassArray.TM. Technology More Sensitive Than Electrophoretic Methods in Detecting Gene Mutations: Automated DNA Analysis System Can Speed Up Microsatellite Analyses. Press Release: Dec. 15. 1997, http://www.sequenom.comlpressrelease.htm.

SEQUENOM Reports on Use of Its DNA MassArray.TM. Technology to Analyze Genes Associated with Alzheimer's Disease and Arteriosclerosis: Technology Has Applications in Drug Development. Press Release: Sep. 22, 1997, http://www.sequenom.comlpressrelease.htm.

SEQUENOM Signs Agreement With Bruker-Franzen Analytik to Develop Mass Spectrometer for DNA Massarray Analysis. Press Release: Jan. 12, 1998. http://www.sequenom.comlpressrelease.htm.

SEQUENOM Uses DNA MassArray.TM. to Sequence Section of Human Cancer-Related p53 GeneM, Press Release: Mar. 27, 1998. http://www.sequenom.comlpressrelease.htm.

Shaler et al.. "Effect of Impurities on the matrix-Assisted Laser Desorption Mass Spectra of Single-Stranded Oligodeoxynucleotides". Anal. Chem. 68:576-579 (1996).

Siuzdak. Gary. "The emergence of mass spectrometry in biochemical research", PNAS USA 91:11290-11297 (1994).

Smith R. D., "New developments in biochemical mass spectrometry: Electrospray Ionization", Anal. Chem. 62:882-899(1990).

Smith. Cassandra L., "cDNA Fingerprinting of Breast Cancer Tumor Cells", Boston Univ., MA. 3-12, (1996).

Solouki et al. "Attomole Biomolecule Mass Analysis by MAtrix-Assisted Laser Desorption/Ionization Fourier Transform Ion Cyclotron Resonance," Anal. Chem. 67:4139-4144 (1995).

Stults and Marsters, "Improved electrospray ionization of synthetic oligodeoxynucleotides", Rapid Comm. Mass Spectrom. 5:359-363 (1991).

Tang et al., "Matrix-assisted laser desorption/ionization mass spectrometry of immobilized duplex DNA probes", Nucleic Acids Research 23:3126-3131 (1995).

Tomer et al., "Coaxial Continuous Flow Fast Atom Bombardment for Higher-Molecular-Weight Peptides: Comparison with Static Fast Atom Bombardment and electrospray Ionization", Bio Mass Spect 20:783-788 (1991).

Trainor, "DNA Sequencing, Automation, and the Human Genome", Anal. Chern. 62:418-426 (1990).

Valaskovic et al. "Attomole Protein Characterization by Capillary Electrophoresis—Mass Spectrometry," Science 273: 1199-1202 (1996).

Valaskovic et al. "Attomole-Sensitivity Electrospray Source for Large-Molecule Mass Spectrometry," Anal. Chem. 67: 3802-3805 (1995).

Vertes A. et al., "Matrix-assisted laser desorption of peptides in transmission geometry", Rapid Comm. in Mass Spect. 4(7):263-266 (1990).

Vorm, et al, Improved Mass Accuracy in Matrix-Assisted Laser Desorption/Ionization Time-Of-Flight Mass Spectrometry of Peptides. Journal of The American Society for Mass Spectrometry, Nov. 1994, V5(N11): 955-958.

Vorm, Ole, et al., Improved Resolution and Very High Sensitivity in MALDI TOF of Matrix Surface Made by Fast Evaporation, Analytical Chemistry, (1994), 3281-3287, 66(19), American Chemical Society.

Wahl et al. "Use of small-diameter capillaries for increasing peptide and protein detection sensitivity in capillary electrophoresis-mass spectrometry," Electrophoresis 14: 448-457 (1993).

Wallace, "Ink-Jet Based Fluid Micro dispensing in Biochemical Applications," Microfab Technologies Inc., Laboratory Automation News, vol. 1, No. 5 pp. 6-9, (1996).

Weiler et al., "Hybridization Based DNA Screening on Peptide Nucleic Acid (PNA) Oligomer Arrays" Nucleic Acids Research, 25(14):2792-2799 1997.

Williams, Time of flight mass spectrometry of DNA laser-ablated from frozen aqueous solutions: applications to the Human Genome Project, Inti. J. Mass Spectrom. and Ion Processes 131 :335-344 {1994}.

Wilm et al. "Electrospray and Taylor-Cone theory, Dole's beam of macromolecules at last," International Journal of Mass Spectrometry and Ion Processes 136: 167-180 (1994).

Wu et al., Matrix-assisted Laser Desorption Time-ot-flight Mass Spectrometry of Oligonucleotides Using 3-Hydroxypicolinic Acid as an Ultraviolet-sensitive Matrix, Rapid Comm Mass Spec 7:142-146 (1993).

Wu et al., "Time-of-Flight Mass Spectrometry of Underivatized Single-Stranded DNA Oligomers by Matrix-Assisted Laser Desorption", Anal. Chem. 66:1637-1645 (1994).

Zhang et al. "Micro-preparation Proceduire for High-sensitivity Matrix-assisted Laser Desorption Ionization Mass Spectrometry," Journal of Mass Spectrometry 30: 1768-1771 (1995).

Zhang et al. "Capillary electrophoresis combined with MALDI-MS spectrometry: continuous deposition on a matrix-precoated membrane target", J. Mass Spectr.,1996, v. 31, No. 9, pp. 1039-1046 (Abstract).

Zuckerman et al., Efficient methods for attachment of thiol specific probes to the 3'-ends of synthetic oligodeoxyribonucleotides, Nucleic Acids Research, 15:13, 5305-5321 (1987).

International Search Report and Written Opinion dated: Apr. 13, 2009 in International Application No. PCT/US2008/076567 filed: Sep. 16, 2008 and published as: WO/2009/039122 on: Mar. 26, 2009.

International Preliminary Report on Patentability dated: Apr. 1, 2010 in International Application No. PCT/US2008/076567 filed: Sep. 16, 2008 and published as: WO/2009/039122 on: Mar. 26, 2009.

International Search Report and Written Opinion dated Feb. 2, 2003 in International Application No. PCT/US2001/45123, filed on Oct. 24, 2001 and published as WO2002/055199 on Jul. 18, 2002.

International Preliminary Examination Report dated Apr. 4, 2003 in International Application No. PCT/US2001/45123, filed on Oct. 24, 2001 and published as WO2002/055199 on Jul. 18, 2002.

(56) References Cited

OTHER PUBLICATIONS

Office Action Mailed: Mar. 19, 1998 for U.S. Appl. No. 08/786,988, filed Jan. 23, 1009 now issued U.S. Pat. No. 7,285,422 issued on Oct. 23, 2007.
Office Action Mailed:Dec. 15, 1998 for U.S. Appl. No. 08/786,988, filed Jan. 23, 1009 now issued U.S. Pat. No. 7,285,422 issued on Oct. 23, 2007.
Office Action Mailed: Mar. 17, 1999 for U.S. Appl. No. 08/786,988, filed Jan. 23, 1009 now issued U.S. Pat. No. 7,285,422 issued on Oct. 23, 2007.
Office Action Mailed: Dec. 7, 1999 for U.S. Appl. No. 08/786,988, filed Jan. 23, 1009 now issued U.S. Pat. No. 7,285,422 issued on Oct. 23, 2007.
Office Action Mailed: Feb. 8, 2001 for U.S. Appl. No. 08/786,988, filed Jan. 23, 1009 now issued U.S. Pat. No. 7,285,422 issued on Oct. 23, 2007.
Office Action Mailed: May 22, 2002 for U.S. Appl. No. 08/786,988, filed Jan. 23, 1009 now issued U.S. Pat. No. 7,285,422 issued on Oct. 23, 2007.
Office Action Mailed: Mar. 18, 2003 for U.S. Appl. No. 08/786,988, filed Jan. 23, 1009 now issued U.S. Pat. No. 7,285,422 issued on Oct. 23, 2007.
Office Action Mailed: Nov. 17, 2003 for U.S. Appl. No. 08/786,988, filed Jan. 23, 1009 now issued U.S. Pat. No. 7,285,422 issued on Oct. 23, 2007.
Office Action Mailed: Jun. 9, 2004 for U.S. Appl. No. 08/786,988, filed Jan. 23, 1009 now issued U.S. Pat. No. 7,285,422 issued on Oct. 23, 2007.
Office Action Mailed: Jan. 14, 2005 for U.S. Appl. No. 08/786,988, filed Jan. 23, 1009 now issued U.S. Pat. No. 7,285,422 issued on Oct. 23, 2007.
Office Action Mailed: Nov. 30, 2005 for U.S. Appl. No. 08/786,988, filed Jan. 23, 1009 now issued U.S. Pat. No. 7,285,422 issued on Oct. 23, 2007.
Office Action Mailed: Jul. 21, 2006 for U.S. Appl. No. 08/786,988, filed Jan. 23, 1009 now issued U.S. Pat. No. 7,285,422 issued on Oct. 23, 2007.
Office Action Mailed: Feb. 23, 2001 for U.S. Appl. No. 09/364,774, filed Jul. 30, 1999 and published as US 2003-0096426 on May 22, 2003, now issued U.S. Pat. No. 7,232,688 issued on Jun. 19, 2007.
Office Action Mailed: Oct. 1, 2002 for U.S. Appl. No. 09/364,774, filed Jul. 30, 1999 and published as US 2003-0096426 on May 22, 2003, now issued U.S. Pat. No. 7,232,688 issued on Jun. 19, 2007.
Office Action Mailed: Feb. 25, 2003 for U.S. Appl. No. 09/364,774, filed Jul. 30, 1999 and published as US 2003-0096426 on May 22, 2003, now issued U.S. Pat. No. 7,232,688 issued on Jun. 19, 2007.
Office Action Mailed: Aug. 13, 2003 for U.S. Appl. No. 09/364,774, filed Jul. 30, 1999 and published as US 2003-0096426 on May 22, 2003, now issued U.S. Pat. No. 7,232,688 issued on Jun. 19, 2007.
Office Action Mailed: Nov. 28, 2003 for U.S. Appl. No. 09/364,774, filed Jul. 30, 1999 and published as US 2003-0096426 on May 22, 2003, now issued U.S. Pat. No. 7,232,688 issued on Jun. 19, 2007.
Office Action Mailed: Sep. 24, 2004 for U.S. Appl. No. 09/364,774, filed Jul. 30, 1999 and published as US 2003-0096426 on May 22, 2003, now issued U.S. Pat. No. 7,232,688 issued on Jun. 19, 2007.
Office Action Mailed: Apr. 13, 2005 for U.S. Appl. No. 09/364,774, filed Jul. 30, 1999 and published as US 2003-0096426 on May 22, 2003, now issued U.S. Pat. No. 7,232,688 issued on Jun. 19, 2007.
Office Action Mailed: Dec. 22, 2005 for U.S. Appl. No. 09/364,774, filed Jul. 30, 1999 and published as US 2003-0096426 on May 22, 2003, now issued U.S. Pat. No. 7,232,688 issued on Jun. 19, 2007.
Office Action Mailed: Jul. 27, 2006 for U.S. Appl. No. 09/364,774, filed Jul. 30, 1999 and published as US 2003-0096426 on May 22, 2003, now issued U.S. Pat. No. 7,232,688 issued on Jun. 19, 2007.
Office Action Mailed: Jan. 29, 2007 for U.S. Appl. No. 09/364,774, filed Jul. 30, 1999 and published as US 2003-0096426 on May 22, 2003, now issued U.S. Pat. No. 7,232,688 issued on Jun. 19, 2007.
Office Action mailed: Oct. 10, 2013 for U.S. Appl. No. 12/123,378, filed May 19, 2008 and published as US 2008-024896 on Oct. 9, 2008.
Office Action mailed: Mar. 28, 2013 for U.S. Appl. No. 12/123,378, filed May 19, 2008 and published as US 2008-024896 on Oct. 9, 2008.
Office Action mailed: Oct. 6, 2009 for U.S. Appl. No. 12/123,378, filed May 19, 2008 and published as US 2008-024896 on Oct. 9, 2008.
Office Action mailed: Mar. 31, 2009 for U.S. Appl. No. 12/123,378, filed May 19, 2008 and published as US 2008-024896 on Oct. 9, 2008.
Office Action dated Apr. 18, 2014 in U.S. Appl. No. 12/123,378, filed May 19, 2008 and published as US 2008-0248968 on Oct. 9, 2008.
Office Action Mailed: Jan. 30, 2008 for U.S. Appl. No. 11/764,711, filed Jun. 18, 2001 and published as US 2008-0008874 on Jan. 10, 2008, now issued U.S. Pat. No. 7,390,672 issued on Jun. 24, 2008.
Office Action Mailed: Apr. 2, 2008 for U.S. Appl. No. 11/764,711, filed Jun. 18, 2001 and published as US 2008-0008874 on Jan. 10, 2008, now issued U.S. Pat. No. 7,390,672 issued on Jun. 24, 2008.
Office Action Mailed: May 11, 2004 for U.S. Appl. No. 10/037,356, filed Oct. 24, 2001, published as US 2002-0142483 on Oct. 3, 2002, now abandoned.
Office Action Mailed: Sep. 1, 2004 for U.S. Appl. No. 10/037,356, filed Oct. 24, 2001, published as US 2002-0142483 on Oct. 3, 2002, now abandoned.
Office Action Mailed: Apr. 4, 2005 for U.S. Appl. No. 10/037,356, filed Oct. 24, 2001, published as US 2002-0142483 on Oct. 3, 2002, now abandoned.
Office Action Mailed: Oct. 23, 2008 for U.S. Appl. No. 11/243,113, filed Oct. 4, 2005 published as US 2006-0024841 on Feb. 2, 2006.
Office Action Mailed: Jun. 29, 2009 for U.S. Appl. No. 11/243,113, filed Oct. 4, 2005 published as US 2006-0024841 on Feb. 2, 2006.
Office Action Mailed: Jan. 5, 2010 for U.S. Appl. No. 11/243,113, filed Oct. 4, 2005 published as US 2006-0024841 on Feb. 2, 2006.
Office Action Mailed: Jul. 8, 2010 for U.S. Appl. No. 11/243,113, filed Oct. 4, 2005 published as US 2006-0024841 on Feb. 2, 2006.
Office Action Mailed: Jan. 18, 2011 for U.S. Appl. No. 11/243,113, filed Oct. 4, 2005 published as US 2006-0024841 on Feb. 2, 2006.
Office Action Mailed: Aug. 19, 2011 for U.S. Appl. No. 11/243,113, filed Oct. 4, 2005 published as US 2006-0024841 on Feb. 2, 2006.
Office Action Mailed: Jan. 23, 2012 for U.S. Appl. No. 11/243,113, filed Oct. 4, 2005 published as US 2006-0024841 on Feb. 2, 2006.
Office Action Mailed: Jun. 26, 2012 for U.S. Appl. No. 11/243,113, filed Oct. 4, 2005 published as US 2006-0024841 on Feb. 2, 2006.
Office Action dated: Apr. 23, 2004 in U.S. Appl. No. 10/117,558, filed Apr. 3, 2002 and published as: 2002/0109085 on: Aug. 15, 2002 and issued as:U.S. Pat. No. 6,812,455 on: Nov. 2, 2004.
Office Action dated: Jan. 14, 2004 in U.S. Appl. No. 10/117,558, filed Apr. 3, 2002 and published as: 2002/0109085 on: Aug. 15, 2002 and issued as:U.S. Pat. No. 6,812,455 on: Nov. 2, 2004.
Office Action dated: Aug. 7, 2003 in U.S. Appl. No. 10/117,558, filed Apr. 3, 2002 and published as: 2002/0109085 on: Aug. 15, 2002 and issued as:U.S. Pat. No. 6,812,455 on: Nov. 2, 2004.
Office Action Mailed: Sep. 12, 2011 for U.S. Appl. No. 12/211,796, filed Sep. 16, 2008 and published as: 2009/0180931 on Jul. 16, 2009.
Office Action Mailed: Apr. 26, 2012 for U.S. Appl. No. 12/211,796, filed Sep. 16, 2008 and published as: 2009/0180931 on Jul. 16, 2009.
Certified English language translation of WO98/03257, Jan. 1998 "Solid supports for analytical measurement methods, their production and their use."
Database WPI, Derwent Publications #198942, citing International PCT Application No. WO 89/09406 published Oct. 5, 1989.
Database WPI, Derwent Publications #199703, citing Japanese Patent No. 8290377 published Nov. 5, 1996.
Database WPI, WPI Acc. No. 98-348616/199830, citing International PCT Application No. WO 98/26179 published Jun. 18, 1998.
Derwent #002061834, WPI Ace. No. 90-302767, for Japanese Application No. JP 2215399, Aug. 1990, Method for detecting DNA—includes de-naturing to single strand, combining with DNA primer having corresp. base sequence forming replicator etc.

(56) References Cited

OTHER PUBLICATIONS

Derwent #011716230, WPI Acc. No. 1998/199813, for PCT Patent Application WO 98/05965 A, Feb. 1998, "Identification of characteristics of eukaryotic cells—after covalent immobilisation on solid support."

Derwent #01201061 , WPI Acc. No. 1998-428971/199837, for German Application No. DE 19731479 A1, Aug. 1998 "Device for analysis of target chemicals has light emitting array—with chemical binder elements attached to array to capture target chemicals which change emitted light pattern accordingly."

Derwent No. 011999582, WPI Ace. No. 1998-416492/199836 for PCT Patent Application WO 98/34116 A1,Aug. 1998, "Isolation and determination of analyte—by capture on specific binding particles and concentration of these on second, limited binding surface before detection, used e.g. for detecting RNA."

English language abstract from Japanese Patent Office for JP-A-8-233710.

English version of Japanese Patent, JP2215399 A 90028 DW9040, WPI Derwent, AN90-302767, Method detect DNA de single strand combination DNA prime correspond base sequence forming replica.

English version of Japanese Patent, JP63230086 A 880926 DW8844, WPI Derwent, AN88-311964, Carry immobilize physiological active substance comprise bind chain form di sulphide compound epoxy group latex contain polymer article.

Sample Preparation—References. pp. 1-3 http address www.chemistry.wustl.edu/.about.mef/damon/samp.sub.-prep.sub.-- references.html from the internet Feb. 2008.

Office Action dated Oct. 17, 2013 in U.S. Appl. No. 13/625,719, filed Sep. 24, 2012 and published as US 2013-0017128 on Jan. 17, 2013.

Office Action dated Feb. 14, 2014 in U.S. Appl. No. 13/625,719, filed Sep. 24, 2012 and published as US 2013-0017128 on Jan. 17, 2013.

Office Action dated Jul. 2, 2014 in U.S. Appl. No. 13/625,719, filed Sep. 24, 2012 and published as US 2013-0017128 on Jan. 17, 2013.

Office Action Mailed: Jun. 13, 2007 for U.S. Appl. No. 08/786,988, filed Jan. 23, 1997 now issued U.S. Pat. No. 7,285,422 issued on Oct. 23, 2007.

Office Action dated Nov. 7, 2013 in U.S. Appl. No. 13/683,214, filed Nov. 21, 2012 and published as US 2013-0079247 on Mar. 28, 2013.

Office Action dated Jun. 19, 2014 in U.S. Appl. No. 13/683,214, filed Nov. 21, 2012 and published as US 2013-0079247 on Mar. 28, 2013.

Office Action dated Oct. 24, 2014 in U.S. Appl. No. 13/683,214, filed Nov. 21, 2012 and published as US 2013-0079247 on Mar. 28, 2013.

Office Action dated Dec. 9, 2014 in U.S. Appl. No. 13/683,214, filed Nov. 21, 2012 and published as US 2013-0079247 on Mar. 28, 2013.

Office Action dated Nov. 24, 2015 in U.S. Appl. No. 14/516,436, filed Oct. 16, 2014 and published as US 2015-0037213 on Feb. 5, 2015.

Office Action dated Jun. 24, 2016 in U.S. Appl. No. 14/516,436, filed Oct. 16, 2014 and published as US 2015-0037213 on Feb. 5, 2015.

Office Action dated Dec. 29, 2016 in U.S. Appl. No. 14/516,436, filed on Oct. 16, 2014 and published as US 2015-0037213 on Feb. 5, 2015.

\* cited by examiner

METHOD AND APPARATUS FOR DELIVERY OF SUBMICROLITER VOLUMES ONTO A SUBSTRATE

RELATED APPLICATIONS

This application is a continuation of U.S. Ser. No. 13/683,214, filed Nov. 21, 2012, which is a continuation of U.S. Ser. No. 11/243,113, filed Oct. 4, 2005, now abandoned, which is a continuation application of U.S. Ser. No. 10/037,356, filed Oct. 24, 2001, now abandoned, which claims benefit of priority under 35 U.S.C. §119 (e) to U.S. provisional application Ser. No. 60/244,404, filed Oct. 30, 2000, to Chao Lin et al., entitled "METHODS AND APPARATUS FOR DELIVERY OF SUBMICROLITER VOLUMES ONTO A SUBSTRATE." The entire disclosure of the above-identified prior applications are considered as being part of the disclosure of the accompanying continuing application and are hereby incorporated in their entirety by reference.

FIELD OF THE INVENTION

The invention relates to sample dispensing systems and, more particularly, to the delivery of liquid samples onto substrate, such as a microarray, for laboratory analysis.

BACKGROUND

Description of the Background Art

Genetic sequencing efforts, such as the Human Genome project, have produced vast amounts of information for basic genetic research that have proven useful in developing advances in health care and drug research. These advances are possible because of improvements in engineering and instrumentation that provide advanced tools for the biotechnology community to continue with basic genetic research. With these advances, scientists can move from basic genomic discoveries to associating specific phenotypes and diseases, and can thereby better identify targets for drug development.

Nucleic acid sequencing and diagnostic methods often analyze samples deposited onto target locations on substrates microarrays, such has microplates, silicon chips and other such supports capable of retaining biological molecules or samples at discrete loci. Microarrays have been used to execute tests on large batches of genetic samples to generate phenotype associations and improve interpretation of the large data sets that result from such tests. A typical microarray, referred to as a chip, includes a substrate, such as a silicon or silicon-coated substrate, on which a large number of reactive points receive samples for testing. Microarray chips provide a technology that permits operators to increase sample throughput, allowing the screening of large numbers of samples and reducing reagent costs by using submicroliter sample volumes. Preparation of such arrays employs a variety of methodologies, including printed arrays and spotted arrays, with a wide variety of substrate surfaces and different modes of quantification. The resulting microarrays are used as substrates for a variety of biochemical applications.

Among the ways for delivery of multiple samples to loci on microarray surfaces are solid pins. The solid pins typically are dipped into a liquid sample, which coats the tip of each pin, holding a sample droplet by surface tension. The coated pins are then touched to a target surface on a microarray substrate, so that the sample is transferred to the target by contact printing. The size and taper of the pin tool tip can affect the volume of liquid sample that is picked up during dipping. The amount of liquid sample transferred on contact will vary with the surface tension of the liquid. Pin tools also can be problematic for high throughput systems because the pins may have to be changed if different sample volumes are desired, or if the nature of the liquid sample is changed to avoid sample contamination. In addition, pin tools cannot be used in situations where contact dispensing where there is a risk of damage to a fragile preloaded sample, such as for mass spectrometric analyses in which samples are deposited on loci that have preloaded material, such as matrix material for matrix-assisted laser desorption (MALDI).

Some mass spectrometry formats, such as MALDI formats, combine the sample to be tested with a matrix material, such as an inorganic acid, which when dried forms a crystal structure. Matrix material can be preloaded on a mass spectrometry substrate and the sample can be added at a later time, using an appropriate liquid dispensing apparatus. When a sample target is preloaded or prespotted with the porous matrix material required for mass spectrometry, direct contact by the solid pin with the matrix material can crush the material.

Other liquid samples dispensing apparatus rely on piezoelectric mechanisms, sometimes using quill-type pin tools that hold the samples in a cut-out at the lower tool tip. Such piezoelectric delivery systems are susceptible to dispensing satellite droplets on a target location because of surface tension effects. Piezoelectric systems also may be prone to variations in voltage and frequency among different tips, which results in variation between the volume of liquid sample dispensed from different individual tips.

From the discussion above, it is apparent that there is a need for a dispensing systems that can accurately deposit precise amounts of liquid sample on target locations on a substrate, with a high throughput rate, without risk of cross contamination of samples or damage to the deposited material. Therefore, it is an object herein to provide apparatus, methods and substrates for fulfilling these and other needs.

SUMMARY OF THE INVENTION

A delivery system for delivery of precise amounts small volumes, particularly submicroliter and smaller volumes is provided. Also provided are pin tools for use in the system and substrates for retaining samples, particularly substrates for use in the systems provided herein.

One delivery system with pin tool as constructed as provided herein, accurately delivers small volumes, typically submicroliter or nanoliter or picoliter volumes, of liquid samples onto a substrates, such as a microarray substrate, at high throughput rates by dipping a slotted pin tool (a pin tool having one or more pins with slotted ends) having an open tip into a sample reservoir or well containing a liquid sample to be delivered onto the substrate, thereby drawing a volume of liquid sample up into the pin tool. The slotted pin tool is then moved toward the substrate at a predetermined rate and then is halted, thereby expelling the liquid sample from the slotted pin tool onto the reaction location of the substrate. Thus, the sample fluid is expelled from the slotted pin tool by the force of momentum. The volume of liquid sample expelled is proportional to the momentum of the moving pin tool (i.e., the amount delivered is proportional to the velocity of the pin tool as it contacts the surface or to the velocity of the liquid in a pin when movement of the pin tool is halted). Hence volume delivered is a function of the speed of moving the pin tool toward the microarray, which provides a way to accurately control and deliver desired sample volumes. For each pin tool size there is a range of volumes in which the amount of volume delivered is a linearly of the velocity of the pin tool. Sample volume delivered is not dependent on tip surface areal, thereby providing for flexibility in use since it is not necessary to change pins to dispense different volumes.

The system uses the slotted pin tool provided herein. The pin tool has a slot that is sufficiently large to contain the volume of sample liquid desired for delivery. The slotted pin tool and system are provided herein. In one aspect, the pin tool slot may be sized to fit around target locations, such as loci on which material has been deposited on a substrate, such as a microarray substrate, to prevent contact between the pin tool and the material. The slotted pins can be mounted in a holding block so as to move up and down in the block; the positions of each pin in the block are selected to match the target loci on the substrate. The slotted pins in the pin tool have a substantially cylindrical tip having a lateral slot forming a cavity with a width of greater than at least about 10, 30, 50, 75 or 100 µm, and can be of a size up to about 300 µm or 500 µm or 1000 µm and having a height of at least about, 25, 50 µm, 100 µm or greater. The selected size is a function of the delivered volume of liquid. Such pins can deliver samples of as low or lower about 1 nanoliter and higher, and can be as low as about 3-10 picoliters.

For example, a pin tool provided herein with a 300 µm slot permits delivery of volumes of as low as about 1 nanoliter to 30 nanoliters. For this pin tool and for delivery of volumes in this range the volume delivered is linearly related to the velocity of the tool prior to halting it. Varying the size of the slot permits greater variation in volume delivered.

The particular geometry of the slot in the pin tool is selected as a function of the size of the loci on the target array. In some embodiments, system is designed so that the pin tool halts prior to contacting the surface. In other embodiments it contacts the surface. For embodiments in which the halting of the movement of the pin tool results from or includes contact with the substrate, the slots fit around each locus.

Generally the sample selected to be delivered, when intended for mass spectrometric analysis by MALDI, results in a spot on the substrate surface that is at least the size of the laser spot but can be smaller or larger as desired. A typical laser spot is about 30-50 µm. Delivery of about 5 nanoliters results in a spot of about 100 µm. The precise size of the spot varies depending upon the surface on which it is delivered.

To move the pin tool towards the substrate, the holding block can be moved toward the substrate, such as a microarray substrate, until the slotted pins on the tool make contact with the microarray, whereupon the pin tool tips fit around the loci, such as spots of matrix material, without contacting any deposited material on the surface. The pin tool then moves upward in the pin tool holding block, which is then moved away from the microarray. Because it is designed to fit around each locus, the pin tool does not contact any material, such as matrix material for MALDI, cells, protein crystals or other materials, on the substrate. In this way, the dispensing system accurately deposits precise amounts of liquid sample on target locations, such as on a microarray substrate, with a high throughput rate, without contacting or damaging any material, such as matrix material, deposited on a substrate.

A microarray substrate that can be used with the system is also provided. This microarray is constructed using photolithographic techniques and hydrophobic materials. Target locations on the microarray are defined with the application of photoresist materials and photolithographic deposition to create an array of locations on the chip that are less hydrophobic than the surrounding areas. The differential hydrophobicity confines the droplets to a desired locus. The microarrays can contain any desired number of loci from 1 to 1000, to 2000 or more, and typically have 96-, 384-, 1536-loci. Higher densities are also contemplated. The pins in the pin tools are in a pattern that matches a selected array.

By virtue of the pin tool design herein, it is possible to transfer the sample to a pre-determined locus on a substrate that already has pre-deposited material, such as matrix, cells, such as bacterial or mammalian cells, protein crystals and other materials sensitive to contact. Since the instant tools provided herein rely on inertial forces for delivery, delivery of liquids is primarily dependent upon the momentum of the liquid in the slotted tool, not on the relative surface tensions of the pin and the substrate for the liquid. As one result, the pin tools provided herein permit accurate and controlled delivery of defined volumes by selection of the velocity of the tool at impact or as it reaches it the substrate and is stopped prior to contact.

Substrates that contain two materials, a photoresist material treated to render it resistant to chemical treatments such as silation used mass spectrometry and other synthetic procedures, and a second more hydrophobic material are provided. Unlike most substrates that employ photolithographic methods, the photoresist is not removed from the surface, but includes the target loci of the surface. This is achieved by baking the substrate. Hence a substrate that contains photoresist material as the target loci are provided.

Also provided are combinations of pin tools that contain slotted pins and substrates, where the number and arrangement of pins and size of the slots is designed to match the arrayed loci and, preferably, the slots are of a size that is greater than each locus, or each locus with loaded or preloaded material, such as matrix material.

Other features and advantages of the apparatus and methods provided herein should be apparent from the following description of preferred embodiments, which illustrate, by way of example, the principles of the methods and apparatus and substrates.

DETAILED DESCRIPTION

Definitions

Figure 1:
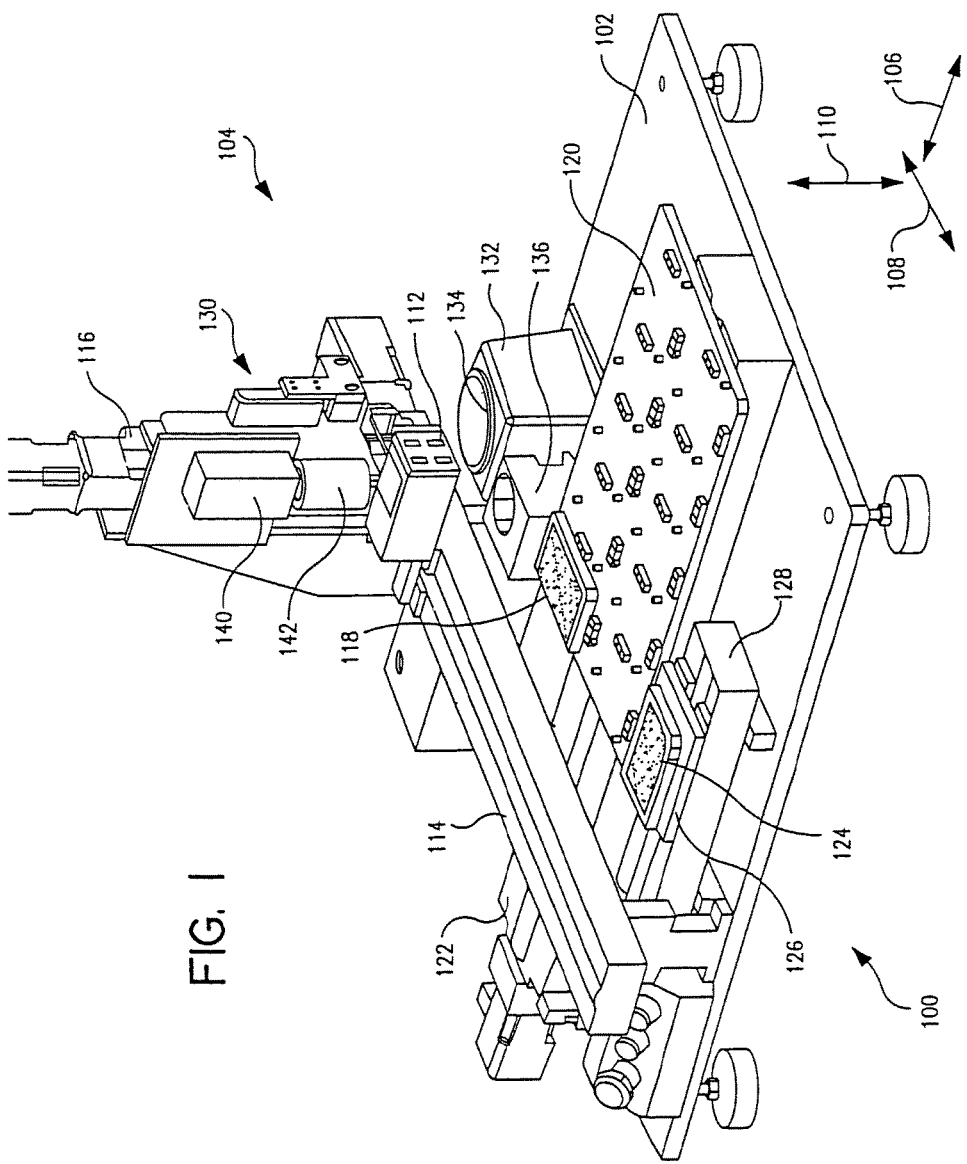
FIG. 1 shows a sample delivery system constructed as provided herein.

Unless defined otherwise, all technical and scientific terms used herein have the same meaning as is commonly understood by one of skill in the art to which this invention belongs. In the event there are different definitions for terms herein, the definitions in this section control. Where permitted, all patents, applications, published applications and other publications and sequences from GenBank and other data bases referred to throughout in the disclosure herein are incorporated by reference in their entirety.

Among the issued patents and published international applications incorporated by reference are: U.S. Pat. Nos. 5,807,522, 6,110,426, 6,024,925, 6,133,436, 5,900,481, 6,043,031, 5,605,798, 5,691,141, 5,547,835, 5,872,003, 5,851,765, 5,622,824, 6,074,823, 6,022,688, 6,111,251, 5,777,324, 5,928,906, 6,225,450, 6,146,854, 6,207,370, International PCT application Nos. WO 99/12040, WO 97/42348, WO 98/20020, WO 98/20019, WO 99/57318, WO 00/56446 and WO 00/60361. These patents and publications describe a variety of mass spectrometric analytical methods, substrates and matrices used in mass spectrometric analyses, and related methods and apparatus, including pin tools and other dispensing systems. It is intended that the methods, substrates, pin tools and delivery systems provided herein are for use in place or addition to the delivery methods, apparatus and substrates described and used in these patents and patent applications. Other intended uses include any methods and assays that use microarrays and other such substrates for syntheses and screening, including sequencing, oligonucleotide and protein syntheses and diagnostic assays, and are particularly suitable for use in high throughput formats.

As used herein, a molecule refers to any molecule or compound that is linked to a substrate. Typically such molecules are macromolecules or components or precursors thereof, such as peptides, proteins, small organics, oligonucleotides or monomeric units of the peptides, organics, nucleic acids and other macromolecules. A monomeric unit refers to one of the constituents from which the resulting compound is built. Thus, monomeric units include, nucleotides, amino acids, and pharmacophores from which small organic molecules are synthesized.

As used herein, macromolecule refers to any molecule having a molecular weight from the hundreds up to the millions. Macromolecules include peptides, proteins, nucleotides, nucleic acids, and other such molecules that are generally synthesized by biological organisms, but can be prepared synthetically or using recombinant molecular biology methods.

As used herein, the term "biopolymer" is used to mean a biological molecule, including macromolecules, composed of two or more monomeric subunits, or derivatives thereof, which are linked by a bond or a macromolecule. A biopolymer can be, for example, a polynucleotide, a polypeptide, a carbohydrate, or a lipid, or derivatives or combinations thereof, for example, a nucleic acid molecule containing a peptide nucleic acid portion or a glycoprotein, respectively. The methods and systems herein, though described with reference to biopolymers, can be adapted for use with other synthetic schemes and assays, such as organic syntheses of pharmaceuticals, or inorganics and any other reaction or assay performed on a solid support or in a well in nanoliter or smaller volumes.

As used herein, a biological particle refers to a virus, such as a viral vector or viral capsid with or without packaged nucleic acid, phage, including a phage vector or phage capsid, with or without encapsulated nucleotide acid, a single cell, including eukaryotic and prokaryotic cells or fragments thereof, a liposome or micellar agent or other packaging particle, and other such biological materials. For purposes herein, biological particles include molecules that are not typically considered macromolecules because they are not generally synthesized, but are derived from cells and viruses.

As used herein, the term "nucleic acid" refers to single-stranded and/or double-stranded polynucleotides such as deoxyribonucleic acid (DNA), and ribonucleic acid (RNA) as well as analogs or derivatives of either RNA or DNA. Also included in the term "nucleic acid" are analogs of nucleic acids such as peptide nucleic acid (PNA), phosphorothioate DNA, and other such analogs and derivatives or combinations thereof.

As used herein, the term "polynucleotide" refers to an oligomer or polymer containing at least two linked nucleotides or nucleotide derivatives, including a deoxyribonucleic acid (DNA), a ribonucleic acid (RNA), and a DNA or RNA derivative containing, for example, a nucleotide analog or a "backbone" bond other than a phosphodiester bond, for example, a phosphotriester bond, a phosphoramidate bond, a phosphorothioate bond, a thioester bond, or a peptide bond (peptide nucleic acid). The term "oligonucleotide" also is used herein essentially synonymously with "polynucleotide," although those in the art recognize that oligonucleotides, for example, PCR primers, generally are less than about fifty to one hundred nucleotides in length.

Nucleotide analogs contained in a polynucleotide can be, for example, mass modified nucleotides, which allows for mass differentiation of polynucleotides; nucleotides containing a detectable label such as a fluorescent, radioactive, luminescent or chemiluminescent label, which allows for detection of a polynucleotide; or nucleotides containing a reactive group such as biotin or a thiol group, which facilitates immobilization of a polynucleotide to a solid support. A polynucleotide also can contain one or more backbone bonds that are selectively cleavable, for example, chemically, enzymatically or photolytically. For example, a polynucleotide can include one or more deoxyribonucleotides, followed by one or more ribonucleotides, which can be followed by one or more deoxyribonucleotides, such a sequence being cleavable at the ribonucleotide sequence by base hydrolysis. A polynucleotide also can contain one or more bonds that are relatively resistant to cleavage, for example, a chimeric oligonucleotide primer, which can include nucleotides linked by peptide nucleic acid bonds and at least one nucleotide at the 3' end, which is linked by a phosphodiester bond, or the like, and is capable of being extended by a polymerase. Peptide nucleic acid sequences can be prepared using well known methods (see, for example, Weiler et al., *Nucleic acids Res.* 25:2792-2799 (1997)).

A polynucleotide can be a portion of a larger nucleic acid molecule, for example, a portion of a gene, which can contain a polymorphic region, or a portion of an extragenic region of a chromosome, for example, a portion of a region of nucleotide repeats such as a short tandem repeat (STR) locus, a variable number of tandem repeats (VNTR) locus, a microsatellite locus or a minisatellite locus. A polynucleotide also can be single stranded or double stranded, including, for example, a DNA-RNA hybrid, or can be triple stranded or four stranded. Where the polynucleotide is double stranded DNA, it can be in an A, B, L or Z configuration, and a single polynucleotide can contain combinations of such configurations.

As used herein, the term "polypeptide," means at least two amino acids, or amino acid derivatives, including mass modified amino acids and amino acid analogs, that are linked by a peptide bond, which can be a modified peptide bond. A polypeptide can be translated from a polynucleotide, which can include at least a portion of a coding sequence, or a portion of a nucleotide sequence that is not naturally translated due, for example, to its location in a reading frame other than a coding frame, or its location in an intron sequence, a 3' or 5' untranslated sequence, a regulatory sequence such as a promoter. A polypeptide also can be chemically synthesized and can be modified by chemical or enzymatic methods following translation or chemical synthesis. The terms "polypeptide," "peptide" and "protein" are used essentially synonymously herein, although the skilled artisan recognizes that peptides generally contain fewer than about fifty to one hundred amino acid residues, and that proteins often are obtained from a natural source and can contain, for example, post-translational modifications. A polypeptide can be post-translationally modified by, for example, phosphorylation (phosphoproteins), glycosylation (glycoproteins, proteoglycans), which can be performed in a cell or in a reaction in vitro.

As used herein, the term "conjugated" refers stable attachment, typically by virtue of a chemical interaction, including ionic and/or covalent attachment. Among preferred conjugation means are: streptavidin- or avidin- to biotin interaction; hydrophobic interaction; magnetic interaction (e.g., using functionalized magnetic beads, such as DYNABEADS, which are streptavidin-coated magnetic beads sold by Dynal, Inc. Great Neck, N.Y. and Oslo Norway); polar interactions, such as "wetting" associations between two polar surfaces or between oligo/polyethylene glycol; formation of a covalent bond, such as an amide bond, disulfide bond, thioether bond, or via crosslinking agents; and via an acid-labile or photocleavable linker.

As used herein, "sample" refers to a composition containing a material to be detected. In a preferred embodiment, the sample is a "biological sample" (i.e., any material obtained from a living source (e.g. human, animal, plant, bacteria, fungi, protist, virus). The biological sample can be in any form, including solid materials (e.g. tissue, cell pellets and biopsies) and biological fluids (e.g. urine, blood, saliva, amniotic fluid and mouth wash (containing buccal cells)). Preferably solid materials are mixed with a fluid. In particular, herein, the sample refers to a mixture of matrix used or mass spectrometric analyses and biological material such as nucleic acids. The pin tools and systems provided herein are designed to dispense nucleic acid compositions into matrix that has been deposited on a substrate or to dispense compositions containing matrix material and biological material such as nucleic acids onto a selected locus or plurality of loci on a substrate.

As used herein, a composition refers to any mixture. It may be a solution, a suspension, liquid, powder, a paste, aqueous, non-aqueous or any combination thereof.

As used herein, a combination refers to any association between among two or more items. The combination can be two or more separate items, such as two compositions or two collections, can be a mixture thereof, such as a single mixture of the two or more items, or any variation thereof.

As used herein, fluid refers to any composition that can flow. Fluids thus encompass compositions that are in the form of semi-solids, pastes, solutions, aqueous mixtures, gels, lotions, creams and other such compositions.

As used herein, the term "solid support" means a non-gaseous, non-liquid material having a surface. Thus, a solid support can be a flat surface constructed, for example, of glass, silicon, metal, plastic or a composite; or can be in the form of a bead such as a silica gel, a controlled pore glass, a magnetic or cellulose bead; or can be a pin, including an array of pins suitable for combinatorial synthesis or analysis.

As used herein, "substrate" refers to an insoluble support onto which a sample and/or matrix is deposited. Support can be fabricated from virtually any insoluble or solid material. For example, silica gel, glass (e.g. controlled-pore glass (CPG)), nylon, Wang resin, Merrifield resin, Sephadex, Sepharose, cellulose, magnetic beads, Dynabeads, a metal surface (e.g. steel, gold, silver, aluminum, silicon and copper), a plastic material (e.g., polyethylene, polypropylene, polyamide, polyester, polyvinylidenedifluoride (PVDF)). Exemplary substrate include, but are not limited to, beads (e.g., silica gel, controlled pore glass, magnetic, Sephadex/Sepharose, cellulose), capillaries, flat supports such as glass fiber filters, glass surfaces, metal surfaces (steel, gold, silver, aluminum, copper and silicon), plastic materials including multiwell plates or membranes (e.g., of polyethylene, polypropylene, polyamide, polyvinylidenedifluoride), pins (e.g., arrays of pins suitable for combinatorial synthesis or analysis or beads in pits of flat surfaces such as wafers (e.g., silicon wafers) with or without plates. The solid support is in any desired form, including, but not limited to: a bead, capillary, plate, membrane, wafer, comb, pin, a wafer with pits, an array of pits or nanoliter wells and other geometries and forms known to those of skill in the art. Preferred support are flat surfaces designed to receive or link samples at discrete loci. Most preferred as flat surfaces with hydrophobic regions surrounding hydrophilic loci for receiving, containing or binding a sample.

As used herein, the term "target site" refers to a specific locus on a solid support upon which material, such as matrix material, matrix material with sample, and sample, can be deposited and retained. A solid support contains one or more target sites, which can be arranged randomly or in ordered array or other pattern. When used for mass spectrometric analyses, such as MALDI analyses, a target site or the resulting site with deposited material, is preferably equal to or less than the size of the laser spot that will be focussed on the substrate to effect desorption. Thus, a target site can be, for example, a well or pit, a pin or bead, or a physical barrier that is positioned on a surface of the solid support, or combinations thereof such as a beads on a chip, chips in wells, or the like. A target site can be physically placed onto the support, can be etched on a surface of the support, can be a "tower" that remains following etching around a locus, or can be defined by physico-chemical parameters such as relative hydrophilicity, hydrophobicity, or any other surface chemistry that retains a liquid therein or thereon. A solid support can have a single target site, or can contain a number of target sites, which can be the same or different, and where the solid support contains more than one target site, the target sites can be arranged in any pattern, including, for example, an array, in which the location of each target site is defined. The pin tools provided herein contain blocks that hold the pins in a pattern that matches the pattern of target sites on a the support, such that upon contacting the support, the ends of the pins surround, but do not touch each loci nor any of the loci.

As used herein, the term "predetermined volume" is used to mean any desired volume of a liquid. For example, where it is desirable to perform a reaction in a 5 microliter volume, 5 microliters is the predetermined volume. Similarly, where it is desired to deposit 200 nanoliters at a target site, 200 nanoliters is the predetermined volume.

As used herein, the term "liquid dispensing system" means a device that can transfer a predetermined amount of liquid to a target site. The amount of liquid dispensed and the rate at which the liquid dispensing system dispenses the liquid to a target site.

As used herein, the term "liquid" is used broadly to mean a non-solid, non-gaseous material, which can be homogeneous or heterogeneous, and can contain one or more solid or gaseous materials dissolved or suspended therein.

As used herein, the term "reaction mixture" refers to any solution in which a chemical, physical or biological change is effected. In general, a change to a molecule is effected, although changes to cells also are contemplated. A reaction mixture can contain a solvent, which provides, in part, appropriate conditions for the change to be effected, and a substrate, upon which the change is effected. A reaction mixture also can contain various reagents, including buffers, salts, and metal cofactors, and can contain reagents specific to a reaction, for example, enzymes, nucleoside triphosphates, amino acids, and the like. For convenience, reference is made herein generally to a "component" of a reaction, wherein the component can be a cell or molecule present in a reaction mixture, including, for example, a biopolymer or a product thereof.

As used herein, submicroliter volume, refers to a volume conveniently measured in nanoliters or smaller and encompasses, for example, about 500 nanoliters or less, or 50 nanoliters or less or 10 nanoliters or less, or can be measured in picoliters, for example, about 500 picoliters or less or about 50 picoliters or less. For convenience of discussion, the term "submicroliter" is used herein to refer to a reaction volume less than about one microliter, although it will be readily apparent to those in the art that the systems and methods disclosed herein are applicable to subnanoliter reaction volumes as well.

As used herein, nanoliter volumes generally refer to volumes between about 1 nanoliter up to less than about 100, generally about 50 or 10 nanoliters.

As used herein, with respect to the supports provided herein, an element is defined as less hydrophobic than another by the relative "wettability" of the element or contact angles, where the contact angle of an element is less than the surrounding surface. The contact angle is the angle the breaks the surface tension when a liquid is delivered. A hydrophilic substrate requires a relatively lower contact angle than a more hydrophobic material. Hence contact angle refers to relative hydrophobicity between or among surfaces.

As used herein, high-throughput screening (HTS) refers to processes that test a large number of samples, such as samples of diverse chemical structures against disease targets to identify "hits" (see, e.g., Broach et al. High throughput screening for drug discovery, *Nature*, 384:14-16 (1996); Janzen, et al. High throughput screening as a discovery tool in the pharmaceutical industry, *Lab Robotics Automation:* 8261-265 (1996); Fernandes, P. B., Letter from the society president, *J. Biomol. Screening,* 2:1 (1997); Burbaum, et al., New technologies for high-throughput screening, *Curr. Opin. Chem. Biol.,* 1:72-78 (1997)]. HTS operations are highly automated and computerized to handle sample preparation, assay procedures and the subsequent processing of large volumes of data.

As used herein, a photoresist refers to a photoresist obtained by polymerization of a diazo photosensitive material with a phenol resin. These photoresists are generally called positive type photoresists.

As used herein, symbology refers to a code, such as a bar code or other symbol, that is engraved, stamped or imprinted on a substrate. The symbology is any code known or designed by the user. In general, the symbols are identifiable to the user or are associated with information stored in a computer or memory and associated with identifying information.

As used herein, the abbreviations for amino acids and protective groups and other abbreviations are in accord with their common usage and, if appropriate, the IUPAC-IUB Commission on Biochemical Nomenclature (see, (1972) *Biochem.* 11: 942-944).

Delivery System

As noted the delivery system provided herein delivers small volumes, typically submicroliter volumes, of liquid samples onto a substrate at high throughput rates by dipping a slotted pin tool having an open tip into a sample reservoir or well containing a liquid sample to be delivered onto a substrate, thereby drawing a volume of liquid sample up into the pins in the pin tool. The pin tool with slotted pin(s) is moved from the sample well to an elevated position above a reaction location on the microarray that is to receive the liquid sample, is lowered toward the substrate at a predetermined speed, and then the movement of the pin tool toward the substrate is halted, thereby expelling the liquid sample from the slotted pin tool onto the reaction location of the substrate, such that the sample fluid is expelled from the slotted pin tool by the force of momentum. The volume of liquid sample expelled is determined by the speed of moving the pin tool toward the microarray. Typically the pin tool contains a plurality of slotted pins. In certain embodiments, the outer surface of the pin is rendered hydrophobic, such as by silanation or other chemical means, relative to the inner surface to thereby reduce or eliminate any satellite drops that adhere to the outer surface.

FIG. 1 depicts an exemplary instrument for pin tool based dispensing. Any such instrument may be adapted for use with the pin tool provided herein. FIG. 1 shows a sample delivery system 100 constructed as described herein. The system 100 includes a base table 102 on which is mounted a transport system 104 having rails or runners that can move a sample in x, y, and z planar coordinates relative to the table and to microtiter plates containing reagents. The x-direction (which will also referred to as left-right) is indicated in FIG. 1 by the arrows 106, the y-direction (also referred to as top-bottom) is indicated by the arrows 108, and the z-direction (also referred to as up-down) is indicated by the arrows 110.

A pin tool holding block 112 is mounted to the transport system 104 for movement in the y-direction along a y-axis rail 114 and for movement in the z-axis direction along a z-axis rail 116. Microtiter plates 118 mounted on an MTP table 120 are moved in the x-axis direction along an MTP rail 122, to move back and forth relative to the pin tool holding block 112. The target microarray chips 124 are mounted on a target table 126 and are moved in the x-axis direction along a target rail 128 for delivery of liquid samples, as described further below.

Figure 2:
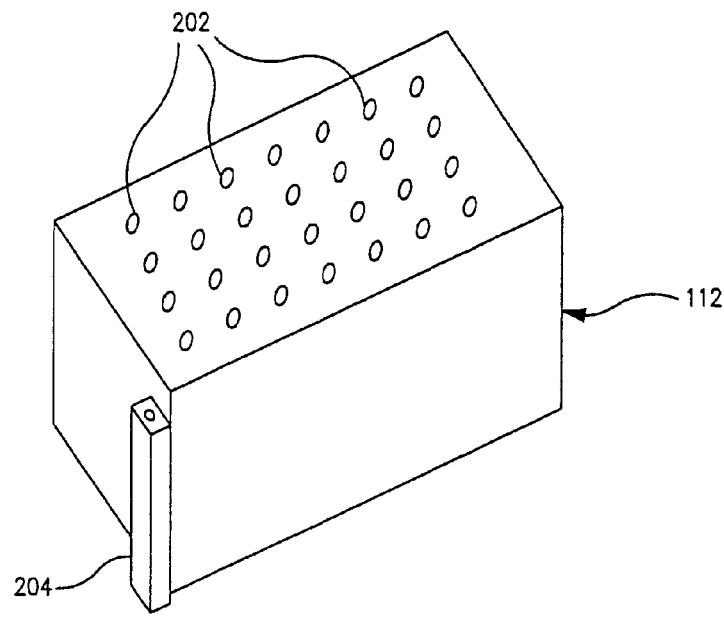
FIG. 2 is a perspective view of a pin tool block and its use in the delivery system shown in FIG. 1.

The pin tool holding block 112 is illustrated in FIG. 2, which shows that the holding block holds a plurality of pin tools 202. The number of pin tools held in the holding block will typically correspond to the number of target locations on the microarray chip 124 (FIG. 1) that will receive samples. In genomic research, for example, a microarray substrate chip may typically contain ninety-six or more target locations. Microarray chips with other numbers of target locations may also be used, such as 384-target arrays or even 1536-target arrays.

The pin tool holding block 112 may also include a single-pin holding station 204, where a single pin tool may be attached. The single holding station permits one pin tool to be easily attached for single-point processing or other special operations involving a single pin tool. The single pin holding station 204 is preferably located on the block 112 such that the single pin tool may be easily accessed for attachment and removal from the pin tool block 112 during normal system operation.

As described further below, the sample delivery system 100 can deliver accurately-controlled volumes of liquid samples onto target locations of a microarray substrate at high throughput rates by dipping a slotted pin tool into a reservoir of liquid sample, thereby drawing a volume of liquid sample up into the pin tool, then moving the slotted pin tool to a position above the substrate, lowering the slotted pin tool toward the substrate at a predetermined speed, and then abruptly halting the movement of the pin tool and expelling the liquid sample from the pin tool onto the substrate. The sample is expelled due to the momentum of the liquid, which is still traveling at the speed of the pin tool when the pin tool is halted. Thus, using the momentum delivery technique described herein, the liquid sample can be deposited onto the microarray substrate without making extended contact with the substrate and without contact between the pin tools and any material at a locus or loci on the substrate.

As described further below, the movement of a pin tool toward the microarray 124 may be halted either because the slotted pin tool makes contact with the microarray, or because the pin tool reaches the limit of travel relative to the pin tool holding block 112. If the pin tool makes contact with the microarray during downward movement of the holding block, then the pin tool is preferably mounted in the block so as to move upwardly independent of the block, so that the pin tool can move up while the block itself is moving downward. In such an arrangement, the pin tool contacts the microarray and the block is stopped in its downward movement substantially simultaneously, followed by lifting up the holding block, carrying the pin tools with it. Alternatively, the pin tool may be moved independently from the block 112 toward the microarray by an actuating mechanism such as a solenoid, halting when the pin tool reaches the limit of travel in the actuating mechanism. These alternatives are described further below.

It has been found that the speed of lowering the pin tool precisely determines the volume of the liquid sample that is expelled. That is, the slot of the pin tool is loaded with liquid sample by dipping, and the portion of that loaded sample that will be expelled is determined by the speed of lowering the pin tool. The momentum delivery technique of the provided herein utilizes any pin tool lowering speed that will impart a momentum force to the liquid sample that is greater than the surface tension of the liquid. The delivery system 100 permits precise control over the speed of moving the pin tool toward the microarray substrate 124. The delivery system thereby carefully controls delivery of the liquid sample, and expels the samples from the pin tools with reduced contamination problems and with increased efficiency and throughput.

Process Steps for Sample Delivery

To deliver the samples to the microarray 124, the pin tool holding block 112 is moved across the table 102 and the pin tools are moved vertically in the z-direction 110 as described above. The pin tool holding block 112 is mounted to an arm 130 of the transport system 104. As the arm 130 moves along the y and z rails 114, 116, the holding block 112 is moved as well, and can thereby be moved across the stations of the table 102 for sample delivery onto microarray substrate chips.

The pin tools are moved first to an ultrasonic cleaning station 132 that includes a cleaning solution bath 134 into which the tips of the pin tools are dipped. The ultrasonic cleaning will typically require approximately five to ten seconds to sufficiently clean the pin tool tips of any remaining samples from prior system operation. When a pin tool is being used on an initial operation, a longer cleaning time is usually necessary, to remove contaminants from the manufacturing process. Such initial cleanings are referred to as preconditioning, and typically require approximately thirty seconds in the ultrasonic bath 134.

The next station of the system 100 is a rinsing and drying station 136. This station includes an empty recess into which the pin tools are lowered, whereupon the recess is filled with a rinse solution, such as distilled water. The rinse bath maintains the pin tool tips in a submerged state for a duration of one to ten seconds, as required for sufficient cleaning of the sample fluid being processed. At the conclusion of the submerged time, the rinse solution is drained, and an air bath is begun, for drying the pin tools. In the preferred embodiment, a vacuum is used in the bottom of the recess to draw off any excess rinse solution and empty the recess. The vacuum drying time is typically on the order of one to ten seconds duration.

Next, the pin tool holding block 112 is moved to a microtiter plate that includes wells containing the liquid sample to be delivered. The holding block is moved from the rinsing and drying station 136 to a position over the MTP table 120. The MTP table may include multiple microtiter plates; only one such microtiter plate 118 is shown in FIG. 1 for simplicity of illustration. Each microtiter plate will preferably contain as many sample wells as there are target locations on the destination microarray 124. The illustrated system 100 has a capacity of ten microtiter plates, as well as a capacity of ten microarray chips, but it should be apparent that different capacities can be easily provided, as desired. A system operator can specify the location of the source microtiter plate 118 in x-y coordinates of the MTP table 120, and also can specify the x-y location of the destination chip 124, with a user control interface described further below, or automatic modes of operation can be implemented to move the pin tools from the various preparatory stations 132, 134 and from one microtiter to the next for continuous processing, as desired. The MTP table 120 will move along the MTP rail 122 and the holding block 112 will move along the y-rail 114 in cooperation to position the desired microtiter plate beneath the holding block.

When the pin tool holding block 112 is located over the appropriate microtiter plate on the MTP table 120, the holding block will be lowered so that the pin tool tips are dipped into the liquid sample contained in the microtiter wells. The volume of liquid sample that will be drawn into the slots of the pin tools will be determined by the size of the slots and the surface tension of the liquid sample. The duration or holding time of the pin tools in the microtiter wells, as well as the speed of lowering, can be selected by the system operator. The duration and speed of dipping will be selected by the operator for the desired sample volume, in accordance with the nature of the sample and factors such as sample viscosity, temperature, and the like.

After the liquid sample has been drawn into each pin tool slot and the pin tool holding block 112 has been raised up from the MTP table 120, the holding block will be moved over an appropriate microarray chip 124 for sample delivery. The chip is located along the microarray chip rail 128, on which multiple chips may be located, and will be moved into proper position for receiving liquid samples. Only one microarray chip 124 is shown in FIG. 1 for simplicity of illustration, but the preferred embodiment permits as many chips to be located on the chip rail 128 as there are microtiter plates 118 on the MTP table 120.

The proper alignment of the pin tools over target locations of the appropriate chip is a critical process, and can be accomplished for example, by the system 100 with a robotic vision unit 140. Initial alignment for a particular pin tool can be accomplished in a number of ways. For example, a camera is mounted on the machine that seeks the target. To align the pin tool with the target loci it is necessary to locate pin(s) relative to the target and/or the pins. To locate the pins, the pins are, for example, dipped into a dye or ink and then contacted with a blank substrate. The camera and software therefor the "learns" or images the locations of the spots and can then direct the pin tool to the corresponding positions on the actual substrate. Alternatively, other marks can be used. Transparent sticky tape can be placed on the surface of the blank substrate and the pin touched thereon to imprint its image on the tape. The camera with software can then learn the locations of the pins. This procedure can also be automated. Such procedure should be performed for each pin tool to create an image thereof so that the loci on the substrate and the pins can be properly aligned.

The robotic vision unit includes a camera 142 that is mounted above the pin tool holding block 112, having a field of view that encompasses at least one corner of the microarray chip that is beneath the holding block. The image that should be observed in the camera field of view when the holding block is properly positioned is known (i.e., see, for example, above). Therefore, the system 100 can confirm proper positioning by comparing the image being received from the camera 142 with the known image that should be obtained.

The system 100, for example, can check for the appearance of a known registration mark that is imprinted on the microarray chip 124, to confirm that the mark is in the expected location, or the system can check for the presence of a target location on the chip that should be in a known position in the camera field of view when there is proper registration of the pin tool block. If the expected registration mark or target location does not appear in the expected position, then the system will issue a warning to the operator and will halt sample processing.

The system may perform a pattern recognition operation to check for proper positioning of the microarray chip and also check for proper chip composition. The image that is obtained in the camera field of view can be compared with the image that should be obtained with a properly produced and aligned chip. Any anomalies in the obtained image may indicate a defective chip, or may indicate that the chip is misaligned. In either case, a warning may be provided and operation of the system may be automatically halted. After the situation with the defective or improperly positioned chip has been corrected, the system operator can indicate to the system that it should continue with normal processing.

If the pin tool holding block 112 is properly positioned, as confirmed by the robotic vision unit 140, then the pin tools are moved toward the microarray chip 124 at a predetermined speed for a time sufficient to impart downward momentum to the liquid sample volumes contained within the slots of the pin tools. The pin tools are then halted in their travel and, because the liquid samples still have downward momentum, the liquid samples keep moving at their imparted speed and therefore are expelled from the pin tools. The liquid samples therefore are simultaneously deposited on the target locations of the chip 124.

After the samples have been deposited on the microarray, the pin tool holding block 112 is moved from its position over the chip 124 and is moved back to the starting point for operations, which is the cleaning station 132. Alternatively, the holding block may be moved to a home position, as commanded by the system operator. The process of cleaning, rinsing and drying, dipping, and expelling may then be repeated, with corresponding movement of the microtiter plates 118 and microarray chips 124 for dipping and expelling, respectively.

System Control

Figure 3:
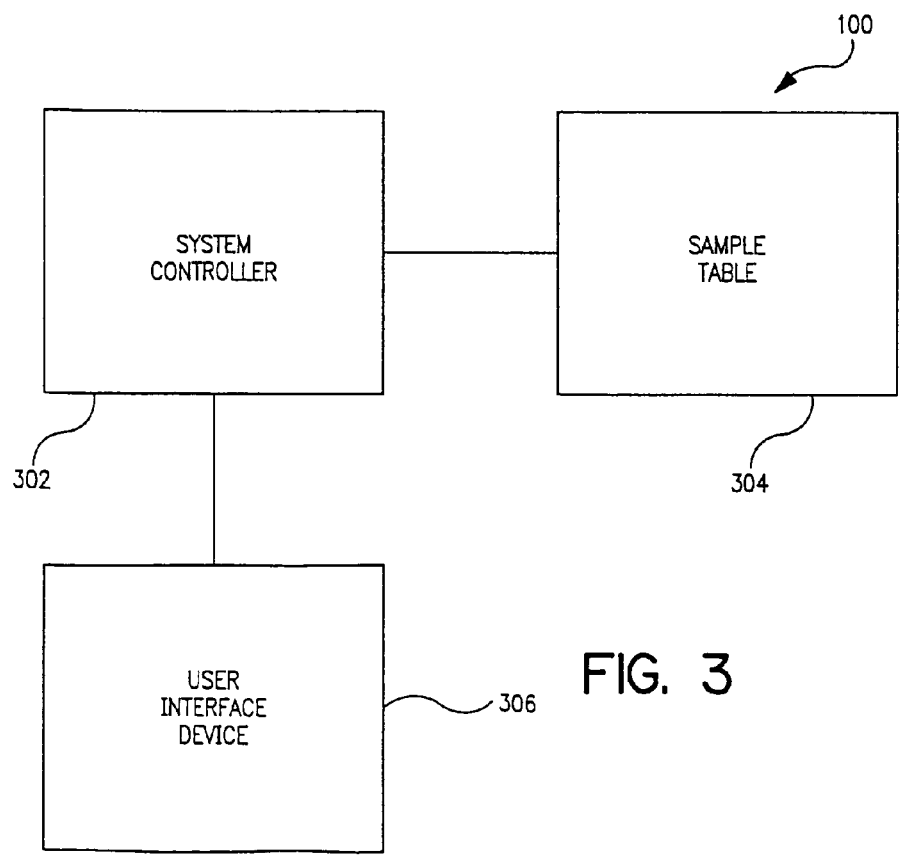
FIG. 3 is a block diagram illustrating the primary components of a delivery system shown in FIG. 1.

FIG. 3 is a schematic block diagram illustrating the primary components of the delivery system shown in FIG. 1. A controller 302 contains a computer processor and associated software and circuitry to communicate with and control the mechanisms of the sample table 304. The sample table 304 as illustrated in FIG. 3 represents the table mechanisms shown in FIG. 1 for moving the pin tools along their respective rails, and for moving the microarray chips along the microtiter rail. The table 304 also includes the mechanisms for controlling the operation of the cleaning station, rinsing and drying station, dipping station, and robotic vision unit described above.

The controller 302 is itself controlled by a user interface device 306, such as a conventional laptop or desktop Personal Computer with application software to provide a graphical user interface. The system operator may adjust the speed of downward pin tool movement and may specify target microarray chips and microtiter plates, as well as other operational parameters, through the user interface device 306.

Pin Tools

The pin tools provided herein are include pins that are slotted such that upon contacting the surface of a substrate with deposited material or other loci, the pin tool contacts the surface of the substrate, but does not touch any of the loci or material deposited thereon. The slotted pins are also provided, as is a block containing or other support containing a plurality of pins in an array or arrangement that matches the array of loci on a target surface.

Figure 4:
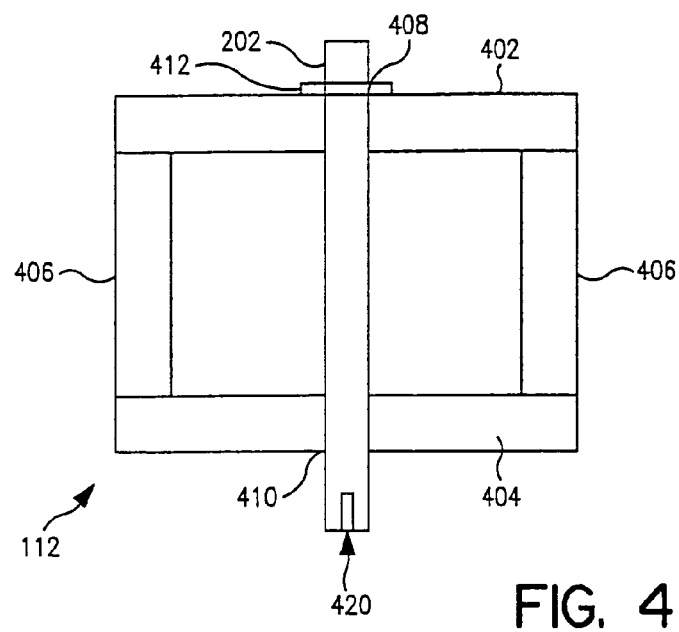
FIG. 4 is a side phantom view of a slotted pin tool in the sample delivery system illustrated in FIG. 1, illustrating a "floating pin" configuration.

The individual pins in the pin tools 202 (FIG. 2) are of slotted construction to work with the momentum delivery technique of the system 100. A pin tool 202 is shown in side section in FIG. 4, illustrating a "floating" pin arrangement. A detail side view of a pin tool tip is shown in FIG. 5 and a plan view through the pin tool tip is shown in FIG. 6.

FIG. 4 shows a pin tool 202 in the pin tool holding block 112 and indicates that the holding block is hollow, having a top wall 402 and bottom wall 404 joined by a side wall 406. It should be understood that only one pin tool is shown for simplicity of illustration, but that the holding block has a greater holding capacity, as described above. The pin tool 202 slides up and down relative to the holding block 112 through an upper guide hole 408 in the top wall 402 and a lower guide hole 410 in the bottom wall 404. A clip 412 attached to the pin tool prevents the pin tool from falling out through the bottom wall. Thus, the pin tool is free to move upwardly in the holding block 112. When the holding block is moved toward the microarray 124, the pin tool is free to make contact with the surface of the microarray without suffering damage and without damaging any material on the microarray, and the holding block 112 can be set to move upward at that point, through the user interface. By permitting upward movement of the pin tool 202 relative to the holding block 112, there is a greater operating margin for setting the point at which the holding block will be moved back upward away from the microarray. This reduces the risk of damage. Moreover, this construction permits the pin tool to be abruptly halted in downward movement (by making contact with the microarray), thereby expelling the liquid sample, without damaging the pin tools or microarray.

When a pin tool 202 makes contact with the microarray, no material deposited on the microarray will be damaged, because the tip of the pin tool has a slotted construction. FIG. 4 shows a slot 420 in the tip of the pin tool. The slot is sized to fit around material deposited at a target location on the microarray.

Figure 5:
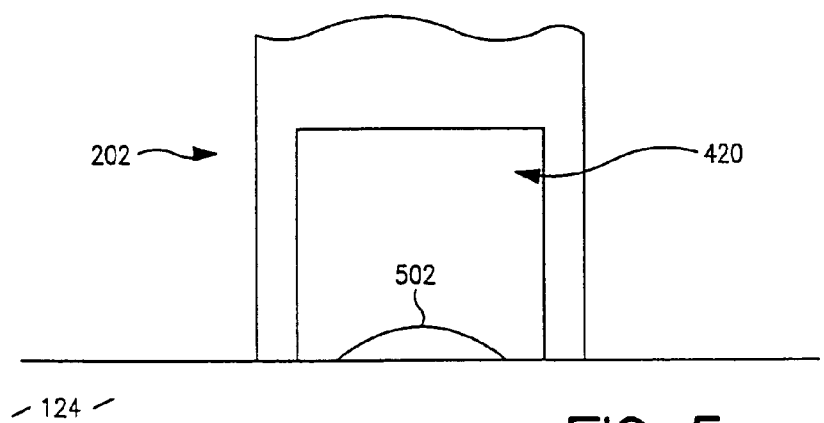
FIG. 5 is a detail side view of a slotted pin tool of the FIG. 1 system.
Figure 6:
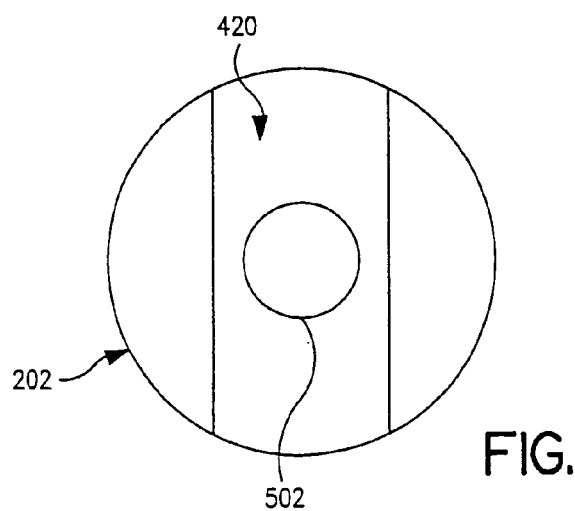
FIG. 6 is a plan view of the slotted pin tool of FIG. 5, looking down through the pin tool toward the microarray substrate.

FIG. 5 shows side detail of a slotted pin tool that is constructed as described herein, and FIG. 6 is a plan view. FIG. 5 and FIG. 6 illustrate how the pin tool preferably fits around the deposited material. In FIG. 5, the pin tool 202 is shown with the slot 420 having sufficient width to permit a mound of material 502 on a microarray 124 to fit within the slot. Other than the slot 420, the pin tool 202 is a solid core construction. FIG. 6 is a plan view, showing that the slot 420 is cut through the pin tool 202 so that the material 502 fits within the slot. Alternatively, the pin tool may be constructed with a hollow core.

For a conventional microarray, the matrix material spots on the microarray surface are typically greater than 100 μm in diameter, and frequently approximately 200 μm in diameter. The distance from the center of one target location (or spot with deposited material, such as matrix for MALDI) to the center of an adjacent target location (or matrix material spot) on the microarray is typically approximately 4.5 mm. Other target spacing may be used as well, including more dense spacing of 2.25 mm from center to center or less dense spacing of 9 mm. Accordingly, the slot 420 preferably has a width of approximately 300 μm, which is a width that provides a sufficient margin of error in positioning of the pin tool and production of the material so that the pin tool safely fits around the typical material spot. The outer diameter of the pin tool is typically approximately 600 μm.

The height of the slot 420 is approximately 5 mm, a height that results in a desired volume of liquid sample being drawn into the slot by capillary action when the pin tool is immersed in the well of a microtiter plate 124 at the MTP table 120 of the system. The system operator will adjust the dipping control mechanism, in concert with the expected depth of reagent in the microtiter wells, through the user interface so that the pin tool is lowered into the microtiter well just below the height of the slot 420 and is raised out of the well before a bubble of air can form in the top of the slot and become trapped. If a bubble is trapped, the volume of liquid sample drawn into the slot may be imprecise, and the volume that is expelled may likewise be imprecise. Thus, FIG. 5 and FIG. 6 show a slotted pin tool 202 that has a slot volume for containing liquid sample of approximate dimensions 300 μm×600 μm×5 mm. The volume of liquid sample drawn into the slot typically contains a volume of between 50 nl and 100 μl. Those skilled in the art will appreciate that this volume represents a larger dispensing volume than obtainable with conventional pin tool delivery systems, thus eliminating evaporation problems that might otherwise arise with smaller sample volumes.

Figure 7A:
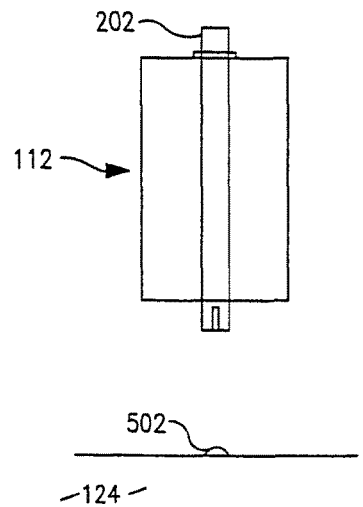
FIGS. 7A, 7B, and 7C are side views of the slotted pin tool showing the liquid sample as drawn into the pin tool and deposited onto the substrate.
Figure 7B:
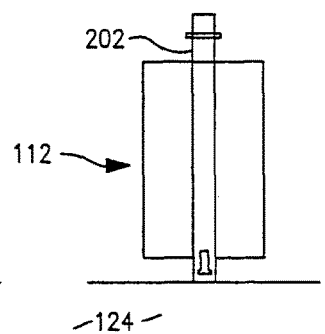
Figure 7C:
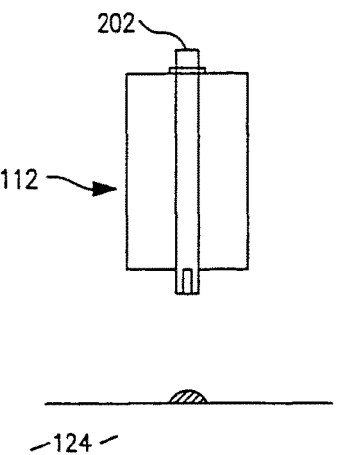

FIGS. 7A, 7B, and 7C are side views of the slotted pin tool 202 showing an operational sequence of the liquid sample after it is drawn into the pin tool and then as it is deposited onto the microarray 124. Only one pin tool is illustrated, but it should be understood that the sequence depicted applies to all the pin tools mounted in the pin tool holding block 112. In FIG. 7A, the pin tool has been dipped into the microtiter well and liquid sample has been drawn into the slot, and the holding block 112 is moving toward the microarray 124.

In FIG. 7B, the pin tool holding block 112 has been lowered sufficiently such that the slotted end of the pin tool has made contact with the microarray surface, fitting around the material as described above. Thus, the downward movement of the pin tool (depicted in FIG. 7A) has been abruptly halted in FIG. 7B. The pin tool floats in the holding block, and therefore the position of the pin tool in FIG. 7B relative to the holding block is somewhat elevated. Due to the momentum of the liquid sample, the liquid continues in the downward direction when the pin tool is halted, expelling the liquid sample out of the pin tool slot and onto the microarray. At approximately the same time when the pin tool makes contact with the microarray, the holding block is moved upward and away from the microarray, thereby eliminating any significant delay in processing. Moving the pin tool block without significant delay increases the system throughput and maintains efficiency. FIG. 7C shows the holding block 112 lifted upward, away from the microarray 124, with the liquid sample remaining behind on the microarray.

Figure 8:
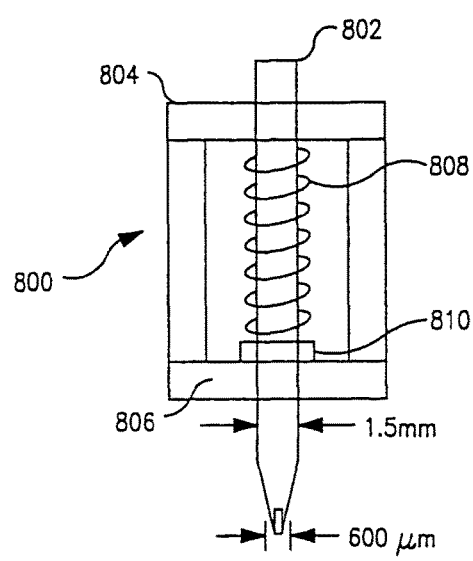
FIG. 8 is a side view of an alternative embodiment of a slotted pin tool for the FIG. 1 system, illustrating a spring-loaded configuration.

FIG. 8 is a side view of an alternative embodiment of a pin tool mounting block 800 and pin tool 802 for the FIG. 1 system, illustrating a spring-loaded configuration. As with the FIG. 4 configuration, the pin tool holding block 800 has a hollow construction, with an upper wall 804 and a bottom wall 806 through which the pin tool 802 may slide up and down. In FIG. 8, however, a spring 808 is attached around the pin tool, between the upper wall and bottom wall. A spring clip 810 fixes the bottom of the spring to a point on the shaft of the pin tool. When the pin tool makes contact with the surface of the microarray 124, the pin tool will begin to move upward in the holding block 800. Because the spring 808 is fixed to the pin tool, the top of the spring is compressed against the upper wall 804, thereby cushioning the upward movement of the pin tool. The spring constant of the spring 808 may be selected for the desired operation and action.

FIG. 8 also shows that a slotted pin tool constructed as described herein may have a tip having a taper, rather than the cylindrical construction of the FIG. 4 embodiment. The FIG. 8 pin tool embodiment, for example, has an outside diameter at the tip of approximately 600 μm, and has an outside diameter at the full extent of the pin tool shaft of approximately 1.5 mm. The greater shaft diameter away from the pin tool tip provides a more durable construction and easier handling, while the narrower tip diameter permits dispensing of small, microliter sample volumes and also denser packing of the pin tool tips. As with the FIG. 4 embodiment, the volume of liquid sample carried by the pin tool 802 will be determined by the volume of the pin tool slot 812. In both the FIG. 4 and FIG. 8 embodiments, the pin tool slot preferably has a width that is typically greater than 200 µm, to fit around material on the microarray, and has a slot height of approximately 100 µm (0.1 mm) to 5 mm, depending on the sample volume desired. The desired volume of liquid sample to be drawn in for delivery will typically be between 50 nl and 100 µl.

In any of the pin tool embodiments described herein, the interior of the pin tool slot may be coated with an ion exchange resin or other resin to assist with cleaning the slot or condition the liquid sample prior to dispensing. The increased size of the pin tool slot illustrated above compared with conventional quill-type pin tools permits reduced manufacturing costs and easier slot inspection for signs of wear. The pin tools provided herein are configured, through controlled downward speed and through spring loading (FIG. 8), such that the pin tools make contact with the microarray surface at a carefully controlled speed, thereby reducing the amount of wear typically experienced by other pin tool configurations.

Figures 9A, 9B, 9C:
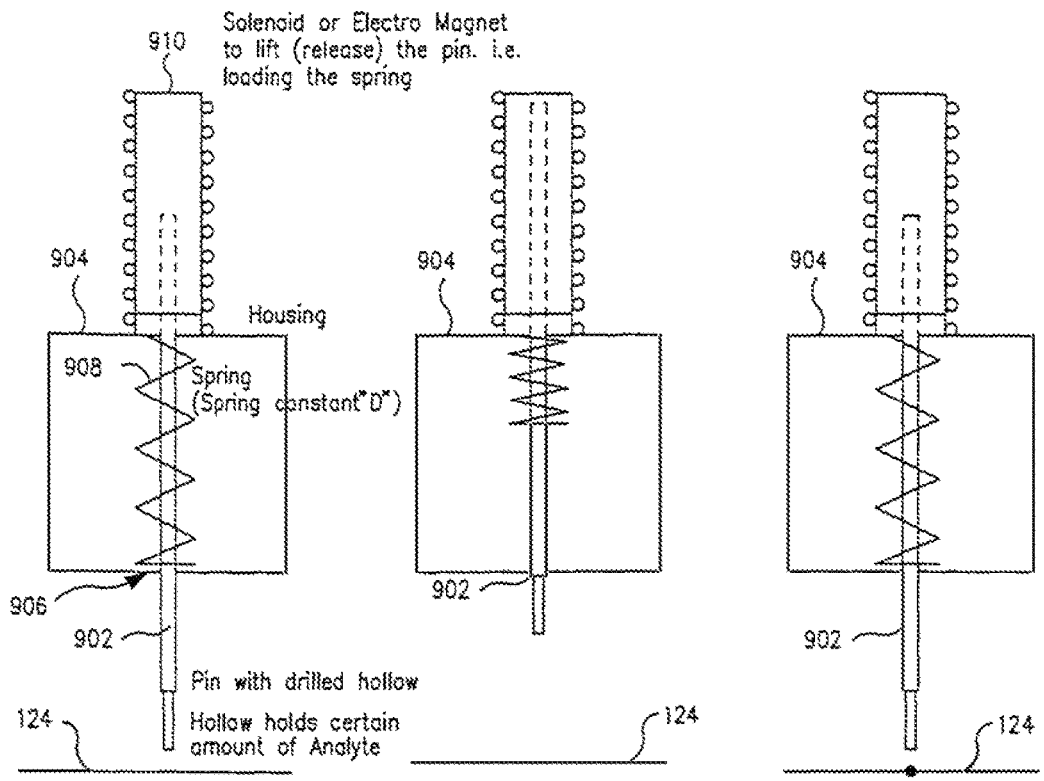
FIGS. 9A, 9B, and 9C are side views of an alternative embodiment of a pin tool for the FIG. 1 system, illustrating a solenoid-activated hollow pin tool.

FIGS. 9A, 9B, and 9C are side views of an alternative embodiment of a pin tool for the FIG. 1 system, illustrating a solenoid-activated hollow pin tool. A metal pin tool 902 or array of pin tools are held in a pin tool holding block 904 by metal e-clips 906. The movement of the pin tool is limited to a vertical direction. The holding block itself can be mounted to any x-y-z station. As shown in FIGS. 9A, 9B, and 9C, the pin tool is spring loaded. A spring 908 having a spring constant "D" is connected to the pin tool and to the holding block, so that the spring can be loaded by pulling the pin tool in the vertical (z) direction. Because both ends of the spring are connected to the holding block and to the pin tool, the pin tool reaches a potential energy $E_{pot(spring)}$ defined by:

$$E_{pot(spring)} = \tfrac{1}{2} D s^2,$$

for a spring constant "D" when shortened by the distance "s". The pin tool itself does not contain a slot, such as illustrated in FIG. 4, but rather has a hollowed opening at its lower tip, similar to the end of a capillary tube. A volume of liquid sample is aspirated into the pin tool using capillary action, when the pin tool is dipped into a microtiter plate or other sample well. The size of the hollowed opening defines the amount of liquid sample that will eventually be dispensed. The volume of sample that fills the hollowed opening of the pin tool by capillary action will be the same as the dispensed volume. This provides an important means of controlling the volume of liquid sample that is dispensed.

Samples are dispensed by loading the spring 908 and bringing the spring to the potential energy level indicated by the equation above. The spring is loaded (FIG. 9B) by mechanical compression or by electromagnetic force such as supplied by a solenoid. In FIG. 9A, FIG. 9B, and FIG. 9C, a solenoid 910 is shown at the top end of the pin tool, but other configurations for loading the spring 908 will occur to those skilled in the art. When the spring is released, the pin tool is moved toward the microarray 124 at a predetermined velocity, given by the equation above, carrying the liquid sample in the hollowed opening and imparting it with the same velocity as the pin tool. When the pin tool reaches the end of its travel, at FIG. 9C, the pin tool stops in the holding block, but the liquid sample continues moving, due to the imparted momentum. Therefore, the liquid sample is expelled from the hollowed opening and is delivered to the microarray via momentum force.

Figure 11:
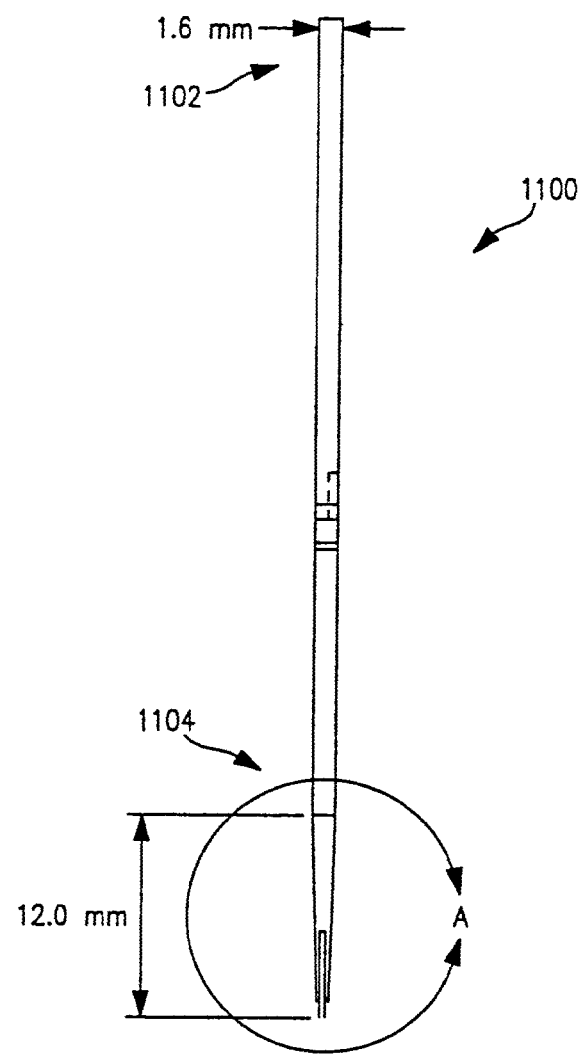
FIG. 11 is a side view of an alternative embodiment of a slotted pin tool having a tapered end permitting entry into very small wells.

FIG. 11 is a side view of an alternative embodiment of a slotted pin tool 1100 constructed as described herein, having a tapered end. As illustrated in FIG. 11, the upper portion 1102 of the pin tool toward the holding block has a nominal outer diameter of approximately 1.6 mm and a length of 63.5 mm. The outer diameter of the pin tool shaft begins to taper from the nominal diameter at a location 1104 approximately 12 mm from the tip of the pin tool. The dimensions of the tapered end, described further below, have been found to provide accurate dispensing of nanoliter and subnanoliter volumes. The taper of the pin tool permits dipping the pin tool into relatively small volume wells without contacting the sidewalls of the wells, thereby permitting small volumes of liquid to be drawn into the pin tool. The taper of the pin tool also decreases the importance of pin tool alignment with the wells, as there is increased clearance between the pint tool and the sidewalls of the wells. The decreased time used for pin tool alignment increases the efficiency of the dispensing system.

Figure 12:
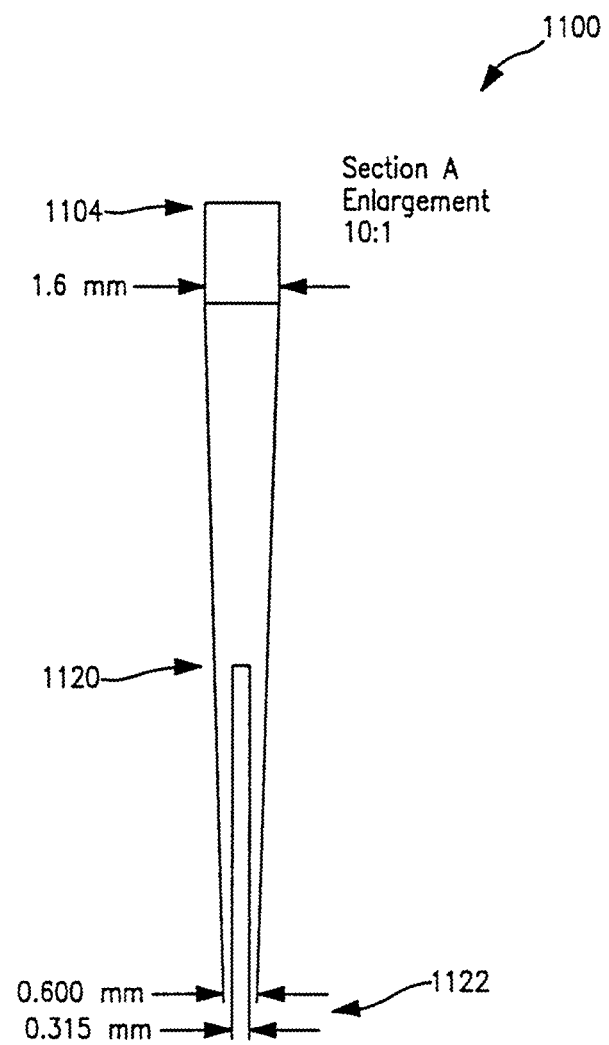
FIG. 12 is an enlarged view of the tip of the pin tool illustrated in FIG. 11.

FIG. 12 shows an enlarged view of the slotted pin tool 1100 illustrated in FIG. 11, showing details of the pin tool tip. The upper location where the taper begins is again indicated by the arrow 1104, approximately 12.0 mm above the pin tool tip. The slot of the pin tool extends from the tip to a location 1120 that may be from approximately 0.1 mm to 5.0 mm above the tip, depending on the sample volume that is to be dispensed. The greater the height of the slot, the greater the volume of sample liquid that can be drawn into the pin tool and dispensed therefrom.

At the pin tool tip 1122, the outer diameter of the pin tool is approximately 0.4 mm to 0.6 mm. The width of the slot is preferably approximately 0.3 mm. These dimensions permit convenient use with sample wells of decreased diameter, and provides increased tolerances for misalignment. The taper from the upper taper location 1104 to the tip 1122 is generally a linear taper, from about 1.6 mm diameter to about 0.6-0.4 mm diameter, such that half of the taper diameter occurs approximately half way between the upper taper point 1104 and the lower taper point 1122. It should be understood, however, that different dimensions and taper configurations may be employed, and are a function of various parameters, including the configuration of sample wells being used and sample volumes that are desired.

Substrates

Any substrate suitable for biological and chemical reactions and assays, such as diagnostic and hybridization assays in which samples are deposited at discrete loci is contemplated for use herein. The loci on the substrates and pin tools are matched so that the pattern of pins and size of the slots matches the arrangement and size of loci with preloaded material thereon. Preferably, the number of pins is the same as the number of loci or the loci are a multiple thereof to permit deposition of material at a plurality of loci. Combinations of the substrates and the pin tools are also provided.

Substrates with microarrays in which a relatively hydrophilic region or contact region is surrounded by a more hydrophobic area and methods for preparation of such substrates are provided herein. The substrate surface is any surface that has an available reactive group, such as —OH or a primary amine, or is derivatized to have such group. Surfaces include but not limited to TEFLON® (polytetrafluoroethylene (PFTE); Trademark, E. I. DuPont), glass, derivatized glass, plastics, silicon, silicon dioxide ($SiO_2$) and any other such materials known to those of skill in the art.

Also provided are methods of producing substrates and the resulting substrates that have contact angles that result in hydrophobic focusing of hydrophilic liquids on loci formed from photoresist materials. The resulting substrates include elements (loci) on a surface that are less hydrophobic than the surrounding surface, where hydrophobicity is measured by the relative wettability (relative contact angel) of the surrounding area compared to each locus (element). The contact angel of each element is less than that of the surrounding surface. To produce such arrays, a surface, such as any of those described herein or known to those of skill in the art to be suitable for linking or retaining macromolecules, including biopolymers, such as silicon or $SiO_2$ is coated with photoresist, covered with a mask that blocks light as loci on the surface, and exposed to light, the photoresist in the unmasked portions is washed off. The resulting surface is baked to render the photoresist stable to chemical treatments such as silation. The surface is then silated. Since the silane does not stick to photoresist, the resulting surface has silated regions that surround the photoresist elements at the loci. Examples 1 and 3 exemplify this process and the resulting substrates with patterned microarrays. The substrates are preferably about 3000 mm×2000 mm, such as 3068 mm×1960 mm, or can be smaller or larger. The number of elements (loci) on each substrate can be any desired number, such as, 8, 16, 24, 96, 384, 1536, higher densities or any convenient number. Other combinations of surface materials in which the contact angel between the two surfaces is less than or equal to 20° C. are contemplated.

The step of baking the photoresist on the target loci is renders the surface resistant to chemical treatments, such as silation. The selection of the temperature and time is selected so that the photoresist does not become too hydrophobic relative to the rest of the surface for liquid to be focussed at the target loci. Baking should be performed at temperatures of about 190-200° C. for at least about 50-70 minutes. The temperature and time are variable and can be empirically determined for the particular photoresist materials and time of baking to obtain the requisite chemical resistance and stability to treatment and hydrophobicity. Both parameters are important for production of surface with the requisite properties so that the surface can be treated and used in analyses, such as mass spectrometry, and the two materials have the appropriate relative hydrophobicity/hydrophilicity to achieve hydrophobic focussing of the droplets on the target loci.

Photoresist Materials for Preparation of the Substrates

Many photoresist materials are known to those of skill in the art and are readily available. For use herein, selection among such material is made and the materials are tested. Select from among the available those that when spun or coated on a surface and baked as described herein have a contact angle of no greater than 70° C. where the surrounding area is about 90° C., or that have a relative contact angle that is less than the surrounding surface that results in a hydrophobic/hydrophilic focussing of sample material on the loci. For example, a differential of at least about 20° C. is suitable for use in substrates intended for mass spectrometric analysis. The differential is such that it provides a wettable surface.

The photoresist is from the class of commercially available diazoquinone containing positive photoresists (see U.S. Pat. Nos. 3,402,044, 2,797,213, 3,148,983, 3,046,118, 3,201,239, 3,046,120, 3,184,310, 3,567,453, 4,550,069, 5,607,816, 5,567,569, 5,561,029, 5,558,983, 5,550,004, 4,491,629, 4,458,994 and many others). Suitable photoresists can be selected by preparing coated substrates as described herein and assessing hydrophobic focusing of a hydrophilic liquid onto the resulting hydrophilic loci, such as by visual analysis of 3-hydroxypicolinic acid (3-HPA) crystals. To make such assessment an aqueous formulation (14.5 nano liters) of 3-HPA is dispensed on and overlapping the loci on the substrate. As the aqueous solvent evaporates it leaves 3-HPA crystals. Successful focusing of the hydrophilic liquid results in a crystal that conforms to the shape of the hydrophilic loci. If the focusing is not successful the crystallization will occur at the site of dispensing, consequently overlapping the loci.

Suitable photoresist compositions for use herein are coatable liquids containing at a diazo photoactive compound with a resin, such as a novolak (phenolic) base resin for increased viscosity, suspended in an organic solvent. The diazonapthaquinone (DNQ) sensitized phenolic resin (known as novolak resin) are widely available for wafer photolithography processes. Such photoresist compositions are well known (see, e.g., U.S. patents cited above; such resins are commercially available from, for example, Shipley Co., Marlboro, Mass. and Clarian Corp., Charlotte, N.C. and others) and any may be employed in the methods herein to produce the substrates provided herein. The most suitable are those that yield the best hydrophobic focusing as described above. For example, AZ111XFS available from Clariant Corp., Charlotte, N.C., contains cresol novolak resin (117520-84-0), 2,1,4-diazonaphthoquinone ester with cumyl phenol, polyvinyl methyl ether, styrene/acrylic polymer in propylene glycol monomethyl ether acetate.

Exemplary Substrate

Figure 10:
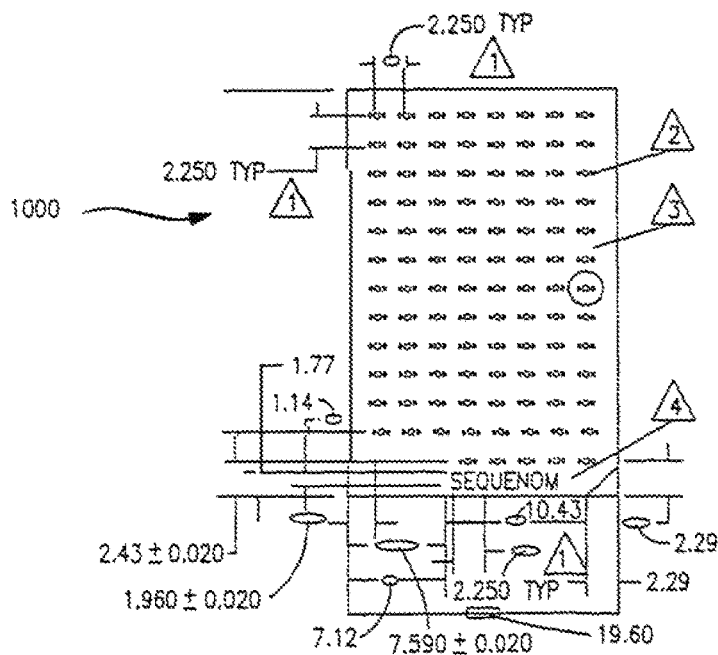
FIG. 10 is a plan view of a microarray substrate for use in the FIG. 1 sample delivery system.

FIG. 10 is a plan view of a microarray substrate 1000 for use in the FIG. 1 sample delivery system. An exemplary substrate 1000 can be constructed using photolithographic techniques and hydrophobic materials as described herein to form target locations (loci) 2 at which, for example, material will be applied and at which liquid samples will be deposited. The target locations 2 on the microarray are defined with the application of photoresist materials and photolithographic deposition such that the target locations on the chip are less hydrophobic than the surrounding areas 3. This differential hydrophobicity reduces the occurrence of satellite droplets that might otherwise extend from the liquid sample and adhere to the microarray surface and permits deposition of small sample amounts.

FIG. 10 shows a 12×8 grid of target locations that have been formed on a 3068 mm×1960 mm surface. Other densities of target locations may be obtained, as desired. The starting surface may be any material that has an available —OH or primary amine, including $SiO_2$ and other forms of glass, plastic, and "TEFLON"-brand materials (Trademark, E. I. DuPont for polytetrafluoroethylene), such as any other material to which the samples, matrix, molecules or biological particles of interest do not adhere, and include any other such materials that are commonly used in the electronics industry to passivate electronic components and circuit boards, and materials used as a coating for medical devices, especially implants, catheters, probes and surfaces of needles. As noted, an element is defined as less hydrophobic than another by the relative "wettability" of the element or contact angles, where the contact angle of an element is less than the surrounding surface. For example, exemplary microarrays with differential hydrophobicity provided herein have $SiO_2$ surfaces with contact angles of 50-55 degrees and contain arrays of target photoresist elements having contact angles of 65 degrees. To create a less hydrophobic environment at each target site, the starting surface was treated with a 3.5% solution of DiMethylDiChloroSilane (DMDCS) from United Chemical Technology of Bristol, Pa., USA in 95% Hexanes from EM Industries, Inc. of Hawthorne, N.Y., USA. The DMDCS does not stick to photoresist and provides a surrounding environment on the substrate whose contact angle is 90 degrees.

With the techniques exemplified below, a target location on the microarray is formed such that the outer area surrounding the target location has a greater hydrophobicity than the inner target area. This increases the accuracy of liquid sample dispensing by reducing or substantially eliminating any satellite droplets from the liquid sample that might adhere to the outer area.

The following examples are included for illustrative purposes only and are not intended to limit the scope of the invention.

Example 1

A flat substrate containing an array of less hydrophobic elements surrounded by more hydrophobic elements, was prepared with an array of photoresist elements. To prepare the array, silicon dioxide ($SiO_2$) was grown on silicon wafers to a height of 3025 angstroms, ±5%. Alternatively, the $SiO_2$ can be grown to a height of about 1050 angstroms. This process is performed by a "wet oxidation" method in which $H_2$ and $O_2$ gases are used in converting the Si to $SiO_2$.

A photoresist material (such as "AZ 111 XFS" photoresist from Clariant Corporation of Charlotte, N.C., USA) was spun onto the $SiO_2$ to a thickness of 0.2 µm to 1.22 µm, with a height of about 1.0 µm. The photoresist was solidified by baking at 65 degrees Celsius for two to three minutes. The surface was then exposed to light of 365 nm wavelength through a mask that blocked light at the target locations. The photoresist that was exposed to light in the unmasked portions of the substrate was then washed off with a phosphoric acid-based developer, leaving an array of photoresist pads having dimensions of approximately 200 µm²×1.0 µm. The wafer was then baked at 195° C. for 60 minutes to remove any remaining solvents. The substrate was then silated with DMDCS. The microarrays can contain any desired number of loci, and typically have 96-, 384-, 1536- loci. Higher densities of loci and densities that are multiples of other than 96 also are contemplated.

In this example, the surface is silicon; any surface that has an available reactive group, such as —OH or a primary amine, including but not limited to TEFLON® (polytetrafluoroethylene (PFTE)), glass, derivatized glass, plastics and other such materials may be used.

Example 2

In another process provided herein, a microarray was produced with a flat starting substrate having an array of $SiO_2$ elements surrounded by a silane surface, thereby creating an array of elements less hydrophobic than the surrounding area. The resulting substrate has target locations that are bare silicon dioxide, and the surrounding regions are silated with DMDCS.

Silicon dioxide was grown on silicon wafers to a height of 3025 Angstroms±5%. Alternatively, the $SiO_2$ can be grown to a height of about 1050 angstroms. This process is performed by a "wet oxidation" method in which $H_2$ and $O_2$ gases are used in converting the Si to $SiO_2$.

The resulting substrate was patterned with "MEGAPOSIT" SPR 900-0.8 photoresist from Shipley Company, L.L.C. of Marlborough, Mass., USA in the manner described above in Example 1. The wafer was then baked at 70° C. for 30 minutes to remove any remaining solvents. The patterned substrate was silated with 3.5% DMDCS for twenty minutes, as described above for Example 1. The photoresist pads were then removed by washing the substrate in acetone for eight minutes at room temperature, thereby dissolving the photoresist and exposing the $SiO_2$. The contact angles of the two materials DMDCS and the bare $SiO_2$ creates a less hydrophobic environment at each target location.

Example 3

In another process, a microarray was produced using a flat substrate having an array of $SiO_2$ elements surrounded by a TEFLON® (polytetrafluoroethylene (PFTE)) surface, to create an array of target elements less hydrophobic than the surrounding area.

Silicon dioxide was grown on silicon wafers to a height of 3025 Angstroms±5%. Alternatively, the $SiO_2$ can be grown to a height of about 1050 angstroms. This process is performed by a "wet oxidation" method in which $H_2$ and $O_2$ gases are used in converting the Si to $SiO_2$.

The resulting substrate was patterned with "MEGAPOSIT" SPR 900-0.8 photoresist from Shipley Company, L.L.C. of Marlborough, Mass., USA as described above for Example 1. The resulting substrate was baked as in Example 2.

The patterned substrate was coated with a TEFLON® (polytetrafluoroethylene (PFTE)) coating, such as "PerFluoroCoat" from Cytonix Company of Beltsville, Md., USA, to a height of 148 to 1200 Angstroms. The photoresist pads were removed by washing the substrate in acetone for eight minutes at room temperature, thereby dissolving the photoresist and exposing the $SiO_2$. The contact angles of the two materials TEFLON® and $SiO_2$ create microarray target locations with a less hydrophobic environment than the surrounding area. For the microarray of Example 3, the TEFLON® (polytetrafluoroethylene (PFTE)) material has a contact angle of 110 degrees, and the $SiO_2$ material has a contact angle of 55 degrees.

In these examples, the areas of differential hydrophobicity on the produced microarray reduces the occurrence of satellite droplets that might otherwise extend from the liquid sample and adhere to the microarray surface, thereby increasing the volume dispensing accuracy.

The methods and apparatus provided herein have been described above in terms of presently preferred embodiments so that an understanding of the present invention can be conveyed. There are, however, many configurations for sample delivery processes and systems not specifically described herein, but with which the present methods and apparatus and disclosure herein is applicable. The present invention should therefore not be seen as limited to the particular embodiments described herein, but rather, it should be understood that the present invention has wide applicability with respect to sample delivery processes and systems generally. All modifications, variations, or equivalent arrangements and implementations that are within the scope of the attached claims should therefore be considered within the scope of the invention.

Since modifications will be apparent to those of skill in this art, it is intended that this invention be limited only by the scope of the appended claims.

The invention claimed is:

1. A substrate for use in mass spectrometric analyses, comprising:
   a solid support comprising silicon or silicon dioxide;
   an array of target locations on a surface of the solid support; each target location of the array consists of a first material which is a positive photoresist material having a first contact angle and which is resistant to silation;

each target location is surrounded by an area on the surface of the solid support comprising a silane having a second contact angle; and the first contact angle is at least about 20 degrees less than the second contact angle.

2. The substrate of claim 1, wherein the silane is dimethyldichlorosilane (DMDCS).

3. The substrate of claim 1, wherein the array consists of 24 target locations.

4. The substrate of claim 1, wherein the array consists of 96 target locations or 384 target locations.

5. The substrate of claim 1, wherein the first contact angle is about 70 degrees.

6. The substrate of claim 1, wherein the solid support comprises a silicon wafer.

7. The substrate of claim 1, wherein the areas surrounding the target locations have a second contact angle of about 90 degrees.

* * * * *